US011000533B2

United States Patent
Daffy

(10) Patent No.: US 11,000,533 B2
(45) Date of Patent: May 11, 2021

(54) CONNECTIVE TISSUE MONITORING, COMPOSITIONS FOR CONNECTIVE TISSUE TREATMENT AND METHODS FOR TREATING CONNECTIVE TISSUE

(71) Applicant: Trackside Technologies Pty Ltd., Kew (AU)

(72) Inventor: John Daffy, Kew (AU)

(73) Assignee: TRACKSIDE TECHNOLOGIES PTY LTD., Kew (AU)

( * ) Notice: Subject to any disclaimer, the term of this patent is extended or adjusted under 35 U.S.C. 154(b) by 0 days.

(21) Appl. No.: 15/864,742

(22) Filed: Jan. 8, 2018

(65) Prior Publication Data

US 2018/0125868 A1    May 10, 2018

Related U.S. Application Data

(63) Continuation-in-part of application No. 14/036,795, filed on Sep. 25, 2013, which is a continuation of
(Continued)

(51) Int. Cl.
*A61K 31/65* (2006.01)
*A61K 31/555* (2006.01)
(Continued)

(52) U.S. Cl.
CPC .............. *A61K 31/65* (2013.01); *A61K 31/12* (2013.01); *A61K 31/352* (2013.01);
(Continued)

(58) Field of Classification Search
CPC .... A61K 31/65; A61K 31/555; A61K 31/573; A61K 31/12; A61K 31/352; A61P 19/04
See application file for complete search history.

(56) References Cited

U.S. PATENT DOCUMENTS 5,310,936 A  *  5/1994  Regtop ................ C07D 209/28
                                                       548/420
6,506,740 B1    1/2003  Ashley et al.
(Continued)

FOREIGN PATENT DOCUMENTS

CA        2728664 A1    12/2009
EP        2286809 A1    2/2011
(Continued)

OTHER PUBLICATIONS

Krady et al., "Minocycline Reduces Proinflammatory Cytokine Expression, Micro glial Activation, and Caspace-3 Activation in a Rodent Model of Diabetic Retinopathy", DIAVETES, vol. 54, May 2005.
(Continued)

*Primary Examiner* — Savitha M Rao
*Assistant Examiner* — Andrew P Lee
(74) *Attorney, Agent, or Firm* — Tarolli, Sundheim, Covell & Tummino LLP

(57) ABSTRACT

A method for treating a non-hemorrhoidal tendon injury in a performance animal in need thereof includes administering to the animal a composition comprising a pro-inflammatory cytokine inhibitor, an antioxidant or catechin, and an anti-inflammatory to thereby treat the non-hemorrhoidal tendon injury in the performance animal.

11 Claims, 7 Drawing Sheets

Related U.S. Application Data application No. PCT/AU2011/000342, filed on Mar. 25, 2011.

(51) Int. Cl.
    *A61K 31/352* (2006.01)
    *A61K 31/573* (2006.01)
    *A61K 31/12* (2006.01)
    *A61P 19/04* (2006.01)

(52) U.S. Cl.
    CPC .......... *A61K 31/555* (2013.01); *A61K 31/573* (2013.01); *A61P 19/04* (2018.01)

(56) References Cited

U.S. PATENT DOCUMENTS

| | | |
|---|---|---|
| 7,204,807 B2 | 4/2007 | Tsoref |
| 2003/0207819 A1 | 11/2003 | Moskowitz |
| 2008/0038377 A1 | 2/2008 | Citow |
| 2008/0108898 A1 | 5/2008 | Meghoufel et al. |
| 2008/0221916 A1 | 9/2008 | Reeves et al. |
| 2009/0221916 A1 | 9/2009 | Konofagou et al. |
| 2012/0225053 A1 | 9/2012 | Dushenkov et al. |

FOREIGN PATENT DOCUMENTS

| | | |
|---|---|---|
| WO | 99/40926 A1 | 8/1999 |
| WO | 1999/040923 A1 | 8/1999 |
| WO | 2010/033800 A2 | 3/2010 |

OTHER PUBLICATIONS

Hossain et al., "Dexamethasone induces apoptosis in proliferative canine tendon cells and chondrocytes", Vet Comp Orthop Traumata/, 2008, pp. 337-342 (Abstract).

Canadian Office Action for Patent Application No. 2,831,101.

European Office Action for Patent Application No. 11862680.3-1112.

Canadian Search Report issued in corresponding foreign application, CA Application No. 2,831,101, pp. 1-6 (dated Jul. 5, 2017).

Dammeier, J., et al., "Dexamethasone is a novel potent producer of connective tissue growth factor expression. Implication for glucocortitoid therapy." Journal of Biological Chemistry 273(29): 18185-18190 (1998).

Van Schie, Hans, T.M., et al., "Monitoring of the repair process of surgically created lesions in equine superficial digital flexor tendons by use of computerized ultrasonography" AJVR 70(1): 37-48 (2009).

Fallon, K., et al., "A "polypill" for acute tendon pain in athletes with tendinopathy" Journal of Science and Medicine in Sport 11 : 235-238 (2008).

Gurney, B., et al., "Absorption of Dexamethasone Sodium Phosphate in human connective tissue using iontophoresis" The American Journal of Sports Medicine 36(4): 753-759 (2008).

European Search Report issued in corresponding foreign application, pp. 1-7 (dated Jul. 21, 2014).

Ianaro, A. et al., "Anti-inflammatory activity of macrolide antibiotics" Journal of Pharmacoloav and Exoerimental Theraoeutics 292(1 ): 156-163 (2000).

Kraus, R.L., et al., "Antioxidant properties of minocycline: neuroprotection in an oxidative stress assay and direct radical-scavenging activity" Journal of Nanochemistry 94: 819-827 (2005).

Sapadin, A.N. et al., "Tetracyclines: Non-antibiotics properties and their clinical implications" J Am Acad Dermatol 54(2): 258-264 (2006).

Yamamoto, T., "Autoimmune mechanisms of scleroderma and a role of oxidative stress" Self/Nonself 2(1 ): 4-10 (2011).

Abuhijleh, Synthesis and characterization of copper-ibuprofenate complexes with 2,2'-bipyridine and 1, 10-phenanthrolines and their hydrolytic activities in phosphate diester cleavage, Polyhedron, 1997, 16(4), pp. 733-740.

Cook, J.L., et al., "Is tendon pathology a continuum? A pathology model to explain the clinical presentation of load-induced tendinopathy" Br J Sports Med 43: 409-416 (2009).

\* cited by examiner

CONNECTIVE TISSUE MONITORING, COMPOSITIONS FOR CONNECTIVE TISSUE TREATMENT AND METHODS FOR TREATING CONNECTIVE TISSUE

RELATED APPLICATION

This application is a Continuation-in-part of U.S. Ser. No. 14/036,795, filed Sep. 25, 2013, which is a Continuation of PCT/AU2011/000342, filed Mar. 25, 2011, the subject matter of which are incorporated herein by reference in their entirety.

FIELD

This invention described herein relates generally to a method for monitoring a connective tissue or part thereof as well as to a composition and method for treating a connective tissue or part thereof. In particular, the invention is directed to a method for monitoring a connective tissue's response to load or part thereof including detecting one or more region of differential structural organisation, although the scope of the invention is not necessarily limited thereto.

BACKGROUND

Athletes, both human and non-human, who present with a connective tissue disease or condition such as, a tendon injury, are particularly problematic to manage clinically. Varying factors such as, the age of the athlete and tendon load leads to idiosyncratic degrees of pain, irritability and capacity to function. The recovery is also variable.

Current treatments are primarily pharmacotherapy and load management. The most commonly used pharmacological agents are non-steroidal anti-inflammatory drugs (NSAIDS). However, most cases do no have the classical features of inflammation. A polypill containing a NSAID, an antibiotic and an antioxidant has been proposed[1].

Improved methods of monitoring connective tissue and treating connective tissue are required.

SUMMARY

The present invention is broadly directed to a method, apparatus and system for monitoring the response to load of a connective tissue or a part thereof, screening a connective tissue or part thereof, classifying a connective tissue or part thereof, a novel composition and a composition for treating a connective tissue or part thereof and a method for treating a connective tissue or part thereof. The invention also provides a method for selecting a pharmacological treatment or a method of designing a training regime for a subject in need of treatment of a connective tissue or condition.

A preferred advantage of the invention is that by monitoring a response to load of a connective tissue or part thereof treatment and training may be selected to minimise any chance of injury, speed recovery and maintain an athlete's ability to compete.

In a first aspect, there is provided a method for monitoring the response to load of a connective tissue or part thereof including the steps of:

obtaining or receiving an ultrasound scan of the connective tissue or part thereof;

analysing the ultrasound scan to detect one or more region of differential structural disorganisation in the connective tissue or part thereof;

classifying the connective tissue or part thereof according to the detected one or more region of differential structural organisation to thereby monitor the response to load of the connective tissue or part thereof.

According to the first aspect, the loading of the connective tissue or part thereof may comprise a tensile or compressive loading.

According to the first aspect, the loading of the connective tissue or part thereof may comprise a training, competitive and/or rehabilitative loading.

According to the first aspect, the ultrasound scan may comprise an axial scan.

According to the first aspect, the ultrasound scan may comprise a series of axial images.

According to the first aspect, the series of images may comprise an image every 0.1 to 10 mm.

Suitably, the series of images comprises an image every 0.5 mm.

According to the first aspect, neighbouring or adjacent images comprised in the ultrasound scan may be associated with respective neighbouring or adjacent areas of the connective tissue or part thereof.

In the first aspect, the differential structural disorganisation may be detected by consistency between axial images.

In the first aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the first aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the first aspect the method may detect an early stage of structural disorganisation in the connective tissue or part thereof.

According to the first aspect the one or more region of differential structural disorganisation may be colour coded.

According to the first aspect, the colour coding may comprise a spectrum correlating with increasing structural disorganisation.

In the first aspect, the connective tissue or part thereof may comprise a human or non-human connective tissue or part thereof.

The non-human may be a performance animal.

The performance animal may be a horse.

According to the first aspect, the method may further comprise selecting a pharmacological treatment based on the response of the connective tissue to load.

In the first aspect, the pharmacological treatment may be based around a competition or race schedule of the subject.

The method of the first aspect may further comprise designing a training and/or exercise regime based on the classification of the connective tissue.

The training regime of the first aspect may comprise treadmill volume prescription, track volume prescription, paddock size implementation strategies and/or weight considerations.

In the first aspect, the connective tissue or part thereof may comprise a performance animal connective tissue or part thereof.

According to the first aspect the connective tissue or part thereof may comprise fibrous connective tissue such as a tendon, ligament or fascia. In preferred embodiments the connective tissue or part thereof may comprise a tendon or part thereof or a ligament or part thereof.

According to the first aspect, the connective tissue or part thereof may comprise an equine superficial digital flexor tendon (SDFT), a deep digital flexor tendon (DDFT), and/or a suspensory ligament.

In the first aspect the method may be a computer method.

In a second aspect the invention provides a method for screening a connective tissue or part thereof for a connective tissue disease or condition associated with response to load including the steps of:

obtaining or receiving an ultrasound scan of a connective tissue or part thereof;

analysing the ultrasound scan to detect one or more region of differential structural disorganisation in the connective tissue or part thereof;

classifying the connective tissue or part thereof according to the detected one or more region of differential structural organisation to thereby screen the connective tissue or part thereof for a connective tissue disease or condition.

According to the second aspect, the loading of the connective tissue or part thereof may comprise a tensile or compressive loading.

According to the second aspect, the loading of the connective tissue or part thereof may comprise a training, competitive and/or rehabilitative loading.

According to the second aspect, ultrasound scan may comprise an axial scan.

According to the second aspect, the ultrasound scan may comprise a series of axial images.

In the second aspect, the series of images may comprise an image every 0.1 to 10 mm.

Suitably, the series of images comprises an image every 0.5 mm.

According to the second aspect, neighbouring or adjacent images comprised in the ultrasound scan may be associated with respective neighbouring or adjacent areas of the connective tissue or part thereof.

In the second aspect, the differential structural disorganisation may be detected by the consistency between axial images.

In the second aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the second aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the second aspect the method may detect an early stage of structural disorganisation in the connective tissue or part thereof.

According to the second aspect the one or more region of differential structural disorganisation may be colour coded.

According to the second aspect, the colour coding may comprise a spectrum correlating with increasing structural disorganisation.

In the second aspect, the connective tissue or part thereof may comprise a human or a non-human connective tissue or part thereof.

The non-human may be a performance animal.

The performance animal may be a horse.

According to the second aspect, the method may further comprise selecting a pharmacological treatment based on the response of the connective tissue or part thereof to load.

In the second aspect, the pharmacological treatment may be based on a competition or race schedule of the subject.

The method of the second aspect may further comprise designing a training and/or exercise regime based on the classification of the connective tissue or part thereof.

The training regime of the second aspect may comprise treadmill volume prescription, track volume prescription, paddock size implementation strategies and/or weight considerations.

According to the second aspect the connective tissue or part thereof may comprise fibrous connective tissue such as a tendon, a ligament or a fascia. In preferred embodiments the connective tissue or part thereof may comprise a tendon or part thereof or a ligament or part thereof.

According to the second aspect, the connective tissue or part thereof may comprise an equine superficial digital flexor tendon (SDFT), a deep digital flexor tendon (DDFT) and/or a suspensory ligament.

In the second aspect the method may be a computer method.

In a third aspect the invention provides a method for classifying a connective tissue or part thereof including the steps of:

obtaining or receiving an ultrasound scan of a connective tissue or part thereof;

analysing the ultrasound scan to detect one or more region of differential structural disorganisation in the connective tissue or part thereof;

classifying the connective tissue or part thereof according to the detected one or more region of differential structural organisation to thereby classify the connective tissue or part thereof.

According to the third aspect, the loading of the connective tissue or part thereof may comprise a tensile or compressive loading.

According to the third aspect, the loading of the connective tissue or part thereof may comprise a training, competitive and/or rehabilitative loading.

According to the third aspect, ultrasound scan may comprise an axial scan.

According to the first aspect, the ultrasound scan may comprise a series of axial images.

According to the third aspect, the axial scan may comprise a series of images.

According to the third aspect, the series of images may comprise an image every 0.1 to 10 mm.

Suitably, the series of images comprises an image every 0.5 mm.

According to the third aspect, neighbouring or adjacent images comprised in the first and second ultrasound scan may be associated with respective neighbouring or adjacent areas of the connective tissue or part thereof.

In the third aspect, the differential structural disorganisation may be detected by the consistency between axial images.

In the third aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the third aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the third aspect the method may detect an early stage of structural disorganisation in the connective tissue or part thereof.

According to the third aspect the one or more region of differential structural disorganisation may be colour coded.

According to the third aspect, the colour coding may comprise a spectrum correlating with increasing structural disorganisation.

In the third aspect, the connective tissue or part thereof may comprise a human or non-human connective tissue or part thereof.

The non-human may be a performance animal.

The performance animal may be a horse.

According to the third aspect, the method may further comprise selecting a pharmacological treatment based on the response of the connective tissue or part thereof to load.

In the third aspect, the pharmacological treatment may be based on a competition or race schedule of the subject.

The method of the third aspect may further comprise designing a training and/or exercise regime based on the classification of the connective tissue or part thereof.

The training regime of the third aspect may comprise treadmill volume prescription, track volume prescription, paddock size implementation strategies and/or weight considerations.

According to the third aspect, the connective tissue or part thereof may comprise a human or non-human connective tissue or part thereof.

In the third aspect, the connective tissue or part thereof may comprise a performance animal connective tissue or part thereof.

According to the third aspect the connective tissue or part thereof may comprise fibrous connective tissue such as a tendon, a ligament or a fascia. In preferred embodiments the connective tissue or part thereof may comprise a tendon or part thereof or a ligament or part thereof.

According to the third aspect, the connective tissue or part thereof may comprise an equine superficial digital flexor tendon (SDFT), a deep digital flexor tendon (DDFT) and/or a suspensory ligament.

In the third aspect the method may be a computer method.

In a fourth aspect the invention provides a computer instruction code for monitoring the response to load of a connective tissue or part thereof, comprising:

computer instruction code operable to obtain or receive an ultrasound scan of a connective tissue or part thereof;

computer instruction code operable to analyse the ultrasound scan to detect one or more region of differential structural disorganisation in the connective tissue or part thereof; and computer instruction code operable to classify the connective tissue or part thereof according to the detected one or more region of differential structural organisation to thereby monitor the response to load of the connective tissue or part thereof.

According to the fourth aspect, the loading of the connective tissue or part thereof may comprise a tensile or compressive loading.

According to the fourth aspect, the loading of the connective tissue or part thereof may comprise a training, competitive and/or rehabilitative loading.

According to the fourth aspect, the ultrasound scan may comprise an axial scan.

According to the fourth aspect, the axial scan may comprise a series of images.

According to the fourth aspect, the series of images may comprise an image every 0.1 to 10 mm.

Suitably, the series of images comprises an image every 0.2 mm.

According to the fourth aspect, neighbouring or adjacent images comprised in the first and second ultrasound scan may be associated with respective neighbouring or adjacent areas of the connective tissue or part thereof.

In the fourth aspect, the differential structural disorganisation may be detected by the consistency between axial images.

In the fourth aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the fourth aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the fourth aspect, an early stage of structural disorganisation in the connective tissue or part thereof may be detected.

According to the fourth aspect the one or more region of differential structural disorganisation may be colour coded.

According to the fourth aspect, the colour coding may comprise a spectrum correlating with increasing structural disorganisation.

In the fourth aspect, the connective tissue or part thereof may comprise human or non-human connective tissue or part thereof.

The non-human may be a performance animal.

The performance animal may be a horse.

According to the fourth aspect, the computer code may further comprise code for selecting a pharmacological treatment based on the response of the connective tissue or part thereof to load.

In the fourth aspect, the pharmacological treatment may be based on a competition or race schedule of the subject.

The fourth aspect may further include designing a training and/or exercise regime based on the classification of the connective tissue or part thereof.

The training regime of the fourth aspect may comprise treadmill volume prescription, track volume prescription, paddock size implementation strategies and/or weight considerations.

In the fourth aspect, the connective tissue or part thereof may comprise a performance animal connective tissue or part thereof.

According to the fourth aspect the connective tissue or part thereof may comprise fibrous connective tissue such as a tendon, a ligament or a fascia. In preferred embodiments the connective tissue or part thereof may comprise a tendon or part thereof or a ligament or part thereof.

According to the fourth aspect, the connective tissue or part thereof may be an equine superficial digital flexor tendon (SDFT), digital flexor tendon (DDFT) and/or a suspensory ligament.

In a fifth aspect the invention provides a computer instruction code for screening a connective tissue or part thereof for a connective tissue disease or condition associated with response to load, comprising:

computer instruction code operable to obtain or receive an ultrasound scan of a connective tissue or part thereof;

computer instruction code operable to analyse the ultrasound scan to detect one or more region of differential structural disorganisation in the connective tissue or part thereof;

and computer instruction code operable to classify the connective tissue according to the detected one or more region of differential structural organisation to thereby screen the connective tissue or part thereof for a connective tissue disease or condition associated with load.

According to the fifth aspect, the loading of the connective tissue or part thereof may comprise a tensile or compressive loading.

According to the fifth aspect, the loading of the connective tissue or part thereof may comprise a training, competitive and/or rehabilitative loading.

According to the fifth aspect, ultrasound scan may comprise an axial scan.

According to the fifth aspect, the ultrasound scan may comprise a series of axial images.

According to the fifth aspect, the series of images may comprise an image every 0.1 to 10 mm.

Suitably, the series of images comprises an image every 0.2 mm.

According to the fifth aspect, neighbouring or adjacent images comprised in the first and second ultrasound scan may be associated with respective neighbouring or adjacent areas of the connective tissue or part thereof.

In the fifth aspect, the differential structural disorganisation may be detected by the consistency between axial images.

In the fifth aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the fifth aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the fifth aspect, an early stage of structural disorganisation in the connective tissue or part thereof may be detected.

According to the fifth aspect the one or more region of differential structural disorganisation may be colour coded.

According to the fifth aspect, the colour coding may comprise a spectrum correlating with increasing structural disorganisation.

In the fifth aspect, the connective tissue or part thereof may comprise a human or non-human connective tissue or part thereof.

The non-human may be a performance animal.

The performance animal may be a horse.

According to the fifth aspect, the computer code may further comprise code for selecting a pharmacological treatment based on the response of the connective tissue or part thereof to load.

In the fifth aspect, the pharmacological treatment may be based on a competition or race schedule of the subject.

The fifth aspect may further comprise designing a training and/or exercise regime based on the classification of the connective tissue or part thereof.

The training regime of the fifth aspect may comprise treadmill volume prescription, track volume prescription, paddock size implementation strategies and/or weight considerations.

According to the fifth aspect the connective tissue or part thereof may comprise fibrous connective tissue such as a tendon, a ligament or a fascia. In preferred embodiments the connective tissue or part thereof may comprise a tendon or part thereof or a ligament or part thereof.

According to the fifth aspect, the connective tissue or part thereof may comprise an equine superficial digital flexor tendon (SDFT), a deep digital flexor tendon (DDFT) and/or a suspensory ligament.

In a sixth aspect the invention provides a computer instruction code for classifying a connective tissue or part thereof including the steps of:

computer instruction code operable to obtain or receive an ultrasound scan of a connective tissue or part thereof;

computer instruction code operable to analyse the ultrasound scan to detect one or more region of differential structural disorganisation in the connective tissue or part thereof;

and computer instruction code operable to classify the connective tissue or part thereof according to the detected one or more region of differential structural organisation to thereby classify the connective tissue or part thereof.

According to the sixth aspect, the loading of the connective tissue or part thereof may comprise a tensile or compressive loading.

According to the sixth aspect, the loading of the connective tissue or part thereof may comprise a training, competitive and/or rehabilitative loading.

According to the sixth aspect, the ultrasound scan may comprise an axial scan.

According to the sixth aspect, the axial scan may comprise a series of images.

According to the sixth aspect, the series of images may comprise an image every 0.1 to 10 mm.

Suitably, the series of images comprises an image every 0.2 mm.

According to the sixth aspect, neighbouring or adjacent images comprised in the first and second ultrasound scan may be associated with respective neighbouring or adjacent areas of the connective tissue or part thereof.

In the sixth aspect, the differential structural disorganisation may be detected by the consistency between axial images.

In the sixth aspect, the classification may be as either healthy, reactive, dysrepair or degenerative.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

The classification may be made in combination with clinical evaluation.

According to the sixth aspect, the one or more region of differential structural disorganisation may be categorised according to the consistency between pixels comprised in the axial image.

The consistency may be between neighbouring or contiguous pixels.

The grayscale value of a pixel may be used to categorize the pixel.

The pixel may be categorized into Category C, Category E, Category B or Category N.

Category C may comprise a pixel correlated as a consequence of constantly high gray values. Categorization into Category C may be indicative of intact fasciculi or correctly aligned fibres showing constantly high gray values.

Category E may comprise a pixel with exclusively entropy as a consequence of rapidly changing gray values over contiguous images. Categorization into Category E may be indicative of an accumulation of cells and/or fibrils.

Category B may comprise a pixel correlated with contiguous images but that also comprises degree of entropy with slight variation. Categorization into Category B may be indicative of incomplete fasciculi or certain steadiness.

Category N may comprise a pixel that did not correlate and did not have entropy. Categorization into Category N may be indicative of homogenous accumulations of fluid or cells.

In the sixth aspect, an early stage of structural disorganisation in the connective tissue or part thereof may be detected.

According to the sixth aspect the one or more region of differential structural disorganisation may be colour coded.

According to the sixth aspect, the colour coding may comprise a spectrum correlating with increasing structural disorganisation.

In the sixth aspect, the connective tissue or part thereof may comprise a human or non-human connective tissue or part thereof.

The non-human may be a performance animal.

The performance animal may be a horse.

According to the sixth aspect, the computer code may further comprise code for selecting a pharmacological treatment based on the response of the connective tissue to load.

In the sixth aspect, the pharmacological treatment may be based on a competition or race schedule of the subject.

The sixth aspect may further comprise designing a training and/or exercise regime based on the classification of the connective tissue or part thereof.

The training regime of the sixth aspect may comprise treadmill volume prescription, track volume prescription, paddock size implementation strategies and/or weight considerations.

According to the sixth aspect the connective tissue or part thereof may comprise fibrous connective tissue such as a tendon, a ligament or a fascia. In preferred embodiments the connective tissue or part thereof may comprise a tendon or part thereof or a ligament or part thereof.

According to the sixth aspect, the connective tissue or part thereof may be an equine superficial digital flexor tendon (SDFT), a deep digital flexor tendon (DDFT) and/or a suspensory ligament.

In a seventh aspect the invention provides a composition comprising an anti-inflammatory, two or more metalloprotease inhibitors, and an inhibitor of cell activity.

The composition may be a slow release composition.

The anti-inflammatory may be a Non-Steroidal Anti-Inflammatory Drug (NSAID).

The NSAID may be ibuprofen, copper ibuprofenate, indomethacin, copper indomethacin, naproxen, flurbiprofen and/or celecoxib.

The two or more metalloprotease inhibitors may comprise a pro-inflammatory cytokine inhibitor and an antioxidant or catechin.

The pro-inflammatory cytokine inhibitor may be an antibiotic such as a tetracycline antibiotic or a macrolide antibiotic.

The antibiotic may be doxycycline, erythromycin, clarythromycin and/or azithromycin.

The antioxidant or catechin may be epigallocatechin gallate (EGCG), green tea extract, fish oil and/or a fish oil extract.

The antioxidant or catechin may be caffeine-free.

The fish oil extract may comprise omega-3-polyunsaturated fatty-acids (n3-PUFA).

The inhibitor of cell activity may also inhibit cell proliferation and/or proteoglycan production.

Suitably the inhibitor of cell activity may be a steroid.

The steroid may be a glucocorticoid steroid.

The glucocorticoid steroid may be dexamethasone.

In one suitable embodiment the composition of the seventh aspect may comprise copper ibuprofenate, doxcycyline, EGCG and dexamethasone.

In an eighth aspect the invention provides a composition comprising a pro-inflammatory cytokine inhibitor and an antioxidant or catechin for use or when used in treating a connective tissue disease or condition in a performance animal.

The performance animal may be equine or canine.

Suitably the performance animal is an equine.

The composition may be a slow release composition.

The pro-inflammatory cytokine inhibitor may be an antibiotic such as a tetracycline antibiotic and/or a macrolide antibiotic.

The antibiotic may be doxycycline, erythromycin, clarythromycin and/or azithromycin.

The antioxidant or catechin may be epigallocatechin gallate (EGCG), green tea extract, fish oil and/or a fish oil extract.

The antioxidant or catechin may be caffeine-free.

The fish oil extract may comprise omega-3-polyunsaturated fatty-acids (n3-PUFA).

The composition of the eighth aspect may further comprise an anti-inflammatory.

The anti-inflammatory may be a Non-Steroidal Anti-Inflammatory Drug (NSAID).

The NSAID may be ibuprofen, copper ibuprofenate, indomethacin, copper indomethacin, naproxen, flurbiprofen and/or celecoxib.

The composition of the eighth aspect may further comprise an inhibitor of cell activity.

The inhibitor of cell activity may also inhibit cell proliferation and/or proteoglycan production.

Suitably the inhibitor of cell activity may be a steroid.

The steroid may be a glucocorticoid steroid.

The glucocorticoid steroid may be dexamethasone.

In one suitable embodiment of the eighth aspect the composition may comprise doxycyline and EGCG.

In another suitable embodiment of the eighth aspect the composition may comprise doxycyline, EGCG and ibuprofen, copper ibuprofenate or indomethacin.

In yet another suitable embodiment of the eighth aspect the composition may comprise doxycyline, EGCG, copper ibuprofenate and dexamethasone.

In a ninth aspect the invention provides a method for treating a connective tissue disease or condition in a non-human subject in need thereof, the method including providing a composition comprising a pro-inflammatory cytokine inhibitor and an antioxidant or catechin to thereby treat the connective tissue disease or condition in the non-human subject.

The non-human subject may be a performance animal.

The performance animal may be an equine or a canine.

Suitably the performance animal is an equine.

The composition may be a slow release composition.

The pro-inflammatory cytokine inhibitor may be an antibiotic such as a tetracycline antibiotic and/or a macrolide antibiotic.

The antibiotic may be doxycycline, erythromycin, clarythromycin and/or azithromycin.

The antioxidant or catechin may be epigallocatechin gallate (EGCG), a green tea extract, fish oil and/or a fish oil extract.

The antioxidant or catechin may be caffeine-free.

The fish oil extract may comprise omega-3-polyunsaturated fatty-acids (n3-PUFA).

The composition provided according to the ninth aspect may further comprise an anti-inflammatory.

The anti-inflammatory may be a Non-Steroidal Anti-Inflammatory Drug (NSAID).

The NSAID may be ibuprofen, copper ibuprofenate, indomethacin, copper indomethacin, naproxen flurbiprofen or celecoxib.

The composition provided according to the ninth aspect may further comprise an inhibitor of cell activity.

The inhibitor of cell activity may also inhibit cell proliferation and/or proteoglycan production.

Suitably the inhibitor cell activity may be a steroid.

The steroid may be a glucocorticoid steroid.

The glucocorticoid steroid may be dexamethasone.

In one suitable embodiment the composition provided according to the ninth aspect may comprise doxycyline and EGCG.

In a tenth aspect the invention provides a method for treating a connective tissue disease or condition in a subject in need thereof, the method including providing a composition comprising an anti-inflammatory, two or more metalloprotease inhibitors and an inhibitor of cell activity to thereby treat the connective tissue disease or condition in the subject.

The subject may be a non-human subject.

The non-human subject may be a performance animal.

The performance animal may be an equine or a canine.

Suitably the performance animal is an equine.

The composition may be a slow release composition.

The anti-inflammatory may be a Non-Steroidal Anti-Inflammatory Drug (NSAID).

The NSAID may be ibuprofen, copper ibuprofenate, indomethacin, copper indomethacin, naproxen, flurbiprofen and/or celecoxib.

The two or more metalloprotease inhibitors may comprise a pro-inflammatory cytokine inhibitor and an antioxidant or catechin.

The pro-inflammatory cytokine inhibitor may be an antibiotic, such as a tetracycline antibiotic and/or a macrolide antibiotic.

The antibiotic may be doxycycline, erythromycin, clarythromycin, and/or azithromycin.

The antioxidant or catechin may be epigallocatechin gallate (EGCG), a green tea extract, fish oil and/or a fish oil extract.

The antioxidant or catechin may be caffeine-free.

The fish oil extract may comprise omega-3-polyunsaturated fatty-acids (n3-PUFA).

The inhibitor of cell activity may also inhibit cell proliferation and/or proteoglycan production.

Suitably the inhibitor of proteoglycan production may be a steroid.

The steroid may be a glucocorticoid steroid.

The glucocorticoid steroid may be dexamethasone.

In one suitable embodiment the composition of the tenth aspect may comprise copper ibuprofenate, doxycyline, EGCG and dexamethasone.

In an eleventh aspect, the invention provides a method for manufacturing a composition according to the seventh or eighth aspects for the treatment of a connective tissue disease or condition.

In a twelfth aspect the invention provides a method for selecting a pharmacological treatment or a method of designing a training regime for a subject in need thereof, the method including scanning a connective tissue or part thereof according to the method of the first aspect or using the computer code of the fourth aspect and based on the comparison selecting the pharmacological treatment or designing the training regime.

In one embodiment of any of the seventh to twelfth aspects, the anti-inflammatory or NSAID may not comprise ibuprofen and/or may comprise copper indomethacin (CuIndomethacin). When the anti-inflammatory or NSAID is copper indomethacin the dose may be 200 mg (⅕ gram) per day or 50 mg to 12 g per day or 50 mg to 50 g per day.

In another embodiment of any of the seventh to twelfth aspects, the proinflammatory cytokine inhibitor may not comprise doxycycline and/or may comprise curcumin. When the a proinflammatory cytokine inhibitor comprises curcumin, the dose may be 450 mg/day with great success or 50 mg to 20 g per day or 50 mg to 50 g per day.

In yet another embodiment of any of the seventh to twelfth aspects, the anti-oxidant or catechin may be caffeine free and/or may comprise EGCG.

In another embodiment of any of the seventh to twelfth aspects, the anti-inflammatory comprises CuIndomethacin, the proinflammatory cytokine inhibitor comprises doxycycline and the anti-oxidant or catechin comprises EGCG.

In still another embodiment of any of the seventh to twelfth aspects, the anti-inflammatory comprises CuIndomethacin, the proinflammatory cytokine inhibitor comprises curcumin and the anti-oxidant or catechin comprises EGCG.

In yet another embodiment of any of the seventh to twelfth aspects, the anti-inflammatory comprises CuIndomethacin, the proinflammatory cytokine inhibitor comprises doxycycline and the anti-oxidant or catechin comprises curcumin.

In still another embodiment of any of the seventh to twelfth aspects, the composition or method achieves or causes an absence of swelling, heat and pain on palpation.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

FIGS. 5A-H show colour representations of the scans shown in FIG. 4A-H.

DETAILED DESCRIPTION

Figure 1:
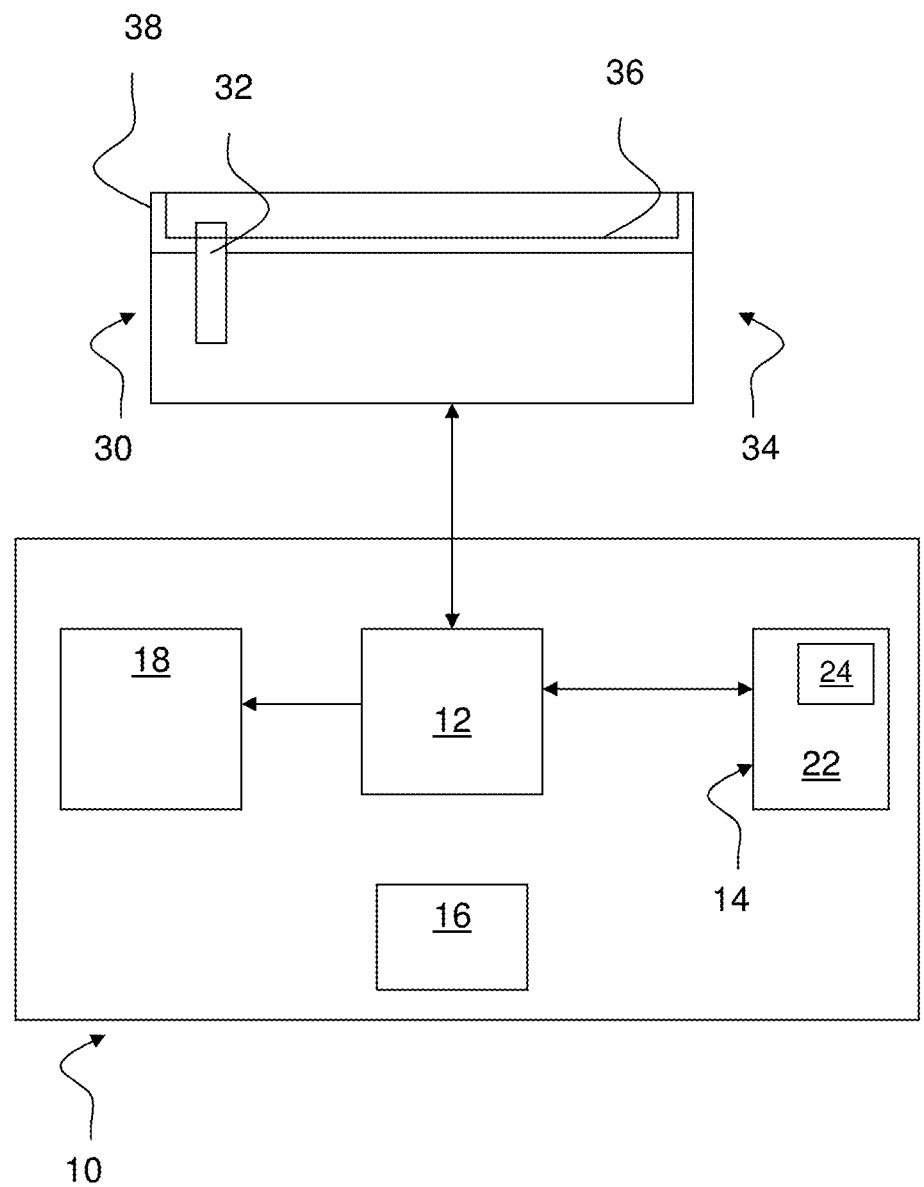
FIG. 1 shows one embodiment of a scanner according to the invention.

The inventors have surprisingly discovered a method for monitoring the response to load of a connective tissue or part thereof. Suitably, the method comprises detecting a region of differential structural disorganisation in the connective tissue or part thereof. Of further surprise is the increased efficacy of the methods and compositions of the invention when applied to a performance animal such as, a horse.

The invention may be applied to any connective tissue disease or condition. Suitable applications include tendinopathy, ligament strain, reactive connective tissue, connective tissue dysrepair and connective tissue degeneration, although the invention is not so limited.

The invention may be applied to any suitable subject. The subject may be an athlete. The athlete may be a human subject or a non-human subject. The non-human subject may be a performance animal such as, an equine or a canine.

The invention may be applied to any connective tissue or part thereof. The connective tissue or part thereof may comprise collagen. Suitably, the connective tissue or part thereof may comprise a tendon or part thereof, a ligament or part thereof, or a fascia or part thereof. A tendon comprises a band of fibrous connective tissue that usually connects muscle to bone and is capable of withstanding tension. A ligament comprises a band of fibrous connective tissue which usually joins one bone to another bone. A fascia comprises a band of fibrous connective tissue which usually connects a muscle to another muscle.

In particular embodiments the connective tissue or part thereof may be an equine superficial digital flexor tendon (SDFT), a deep digital flexor tendon (DDFT) and/or a suspensory ligament.

The load applied to the connective tissue or part thereof may comprise a tensile or compressive load. The load may also comprise a training, competitive and/or rehabilitative load.

The invention will be described below with reference to a tendon. However, the invention is not so limited and instead applies to all connective tissue.

It has been accepted knowledge in the veterinary field that horse tendon injuries cause "lesions." These "lesions" are said to be changes that occur as a result of tearing of collagen, often leading to a classic "core" lesion. The "core" lesion, which occurs in the central part of the tendon and occurs over a variable length of the tendon, causes a hypoechoic area on ultrasound. Other researchers have hypothesized that this central tendon "lesion" is an area of degeneration due to factors such as high temperature or even a lack of blood supply to the centre of the tendon. All of these hypotheses have been based on assumptions and no formal histological studies have been performed to support these hypotheses up to this point The inventors have proposed a new evidence based model for connective tissue injury. Although not wanting to be bound by any one theory, the inventors' model holds that connective tissue can go through four stages, classified as: healthy; reactive; dysrepair; and degenerative. Connective tissue may transition from reactive to dysrepair and back to normal but it may not be possible that a connective tissue return to normal from the final degenerative state.

Surprisingly, the present inventors have discovered that connective tissue may transition through three of theses stages of pathology, namely healthy; reactive and dysrepair. The final degenerative stage may be a state of degeneration where the structure of the connective tissue is irretrievably disrupted. Non-pathological connective tissue is classified as healthy.

Briefly, while not wanting to be bound by any one theory, a reactive connective tissue may have an increase in cell activity and possibly cell numbers with an increase in protein production, particularly large proteoglycans. This increase in proteoglycans binds water and separates the collagen fibrils, resulting in swollen connective tissue. The activated cells produce nociceptive substances, making the connective tissue painful. With correct treatment and load management, the pathology is completely reversible.

A connective tissue in the state of dysrepair is a connective tissue that has been reactive, but the process is driven further by further loading and or failure to intervene. Connective tissue dysrepair is an active reparative state and the connective tissue may recover normal structure with correct treatment early in this phase. In the phase of connective tissue dysrepair, the swelling begins to disrupt the collagen fibrils and the collagen matrix begins to disintegrate. In this state, the greater the matrix degradation, the more opportunity for neovascular ingrowth.

This highlights one of the significant advantages of the present invention, that is, that by monitoring the connective tissue according to the invention the stage of the connective tissue can be identified and the correct method of treatment may be applied before irreparable damage is done. This is especially true of a reactive connective tissue. As such the present invention is particularly significant when the connective tissue is that of an athlete, either human or performance animal, where significant earnings and prestige depend upon a healthy connective tissue.

Further on in the pathology continuum is degeneration of the connective tissue. Here the changes seen in the preceding stages become greater. The collagen matrix is further disrupted, with areas that have little collagen continuity, offering further opportunity for vascular ingrowth. The cells can continue to be active and produce all the proteins to reconstruct the matrix, although in areas of the connective tissue the cells can die, leaving acellular areas with no capacity to repair.

Clinically, reactive connective tissue can be detected in horses when the connective tissue begins to become pathological, although there is evidence that areas of pathology can occur without clinical signs. However, knowing how the connective tissue is responding to treatment can be very difficult to detect clinically and only a gross indication can be given. Therefore, connective tissue imaging is essential to guide diagnosis and rehabilitation.

Surprisingly, and of significant advantage, the inventors have discovered that an acute bowed tendon in a horse behaves like an acute reactive tendon in a human would behave. The reactive tendon may be characterized by increased amounts of proteoglycan, which are very large molecules that attract water and give the tendon its swollen bowed appearance. The bowing occurs often 2-3 days after an overload situation, which is the amount of time it takes for large proteoglycans such as aggrecan to be produced.

The present inventors are the first to discover the pathology outlined above, including the different stages of connective tissue pathology, as opposed to the conventionally accepted model of collagen tearing. The present inventors are also the first to discover that this pathology is occurring in the horse.

Although not wanting to be bound by any one theory, according to the present invention, there is no tear, there is no hole as standard vet practice believes. These areas of altered echogenicity are occurring due to increased proteoglycan and water and do not represent an actual hole within the connective tissue.

Although clinical perspective using examination and history can give a guide to the stage of pathology, imaging the connective tissue with ultrasound will clearly define the classification of connective tissue. Standard ultrasound can diagnose pathology, but lacks capacity to quantify pathology.

The invention makes use of an ultrasound scanner that is able to take a scan of a connective tissue or part thereof which may comprise many images, each image associated with an area of the connective tissue or part thereof scanned. Neighbouring or adjacent images comprised in the scan may be associated with respective neighbouring or adjacent areas of the connective tissue or part thereof. One embodiment of a scanner 30 according to the invention is shown in FIG. 1. Scanner 30 may be operatively connected to computer 10.

In the embodiment shown in FIG. 1, scanner 30 is an Ultrasound Tissue Characterisation (UTC) scanner, available from UTC Imaging BV, is used to scan the connective tissue or part thereof.

The computer 10 may be a laptop or notebook computer. FIG. 1 shows one embodiment of computer 10. A processor 12 is operatively coupled to a storage medium in the form of a memory 14. One or more input device 16, such as a keyboard, mouse and/or pointer, is operatively coupled to the processor 12 and one or more output device 18, such as a computer screen, is operatively coupled to the processor 12.

Memory 14 comprises a computer or machine readable medium 22, such as a read only memory (e.g., programmable read only memory (PROM), or electrically erasable programmable read only memory (EEPROM)), a random access memory (e.g. static random access memory (SRAM), or synchronous dynamic random access memory (SDRAM)), or hybrid memory (e.g., FLASH), or other types of memory as is well known in the art. The computer readable medium 22 comprises computer readable program code 24 for performing the methods in accordance with the teachings of the present invention, at least some of which are selectively executed by processor 12 and are configured to cause the execution of the embodiments of the present invention described herein. Hence, the machine readable medium 22 may have recorded thereon a program of instructions for causing the computer 10 to perform methods in accordance with embodiments of the present invention described herein.

Scanner 30 settings, such as gain, focus and depth, may be standardised to ensure repeatability when re-imaging connective tissue.

Scanner 30 comprises a transducer 32. In one embodiment the transducer comprises a 10 MHz linear-array transducer connected to computer 10. Based on the teachings herein a skilled person is readily able to select other suitable transducers for use in the invention, such as a 5, 15, 20, 25 or 30 MHz transducer. Suitably the transducer is a 5 to 25 MHz transducer.

Transducer 32 may be housed in a transverse position within a custom designed tracking device 34 comprised within scanner 30. Tracking device 34 may comprise a scanning zone 36 within which transducer 32 may move axially so as to scan a length of the connective tissue or part thereof.

The scanning zone 36 may be and the scan may cover 1 to 50 cm; 2 to 40 cm; 3 to 30 cm; or 5 to 20 cm. The scanning zone may be 1, 2, 3, 4, 5, 6, 7, 8, 9, 10, 11, 12, 13, 14, 15, 16, 17, 18, 19, 20, 21, 22, 23, 24, 25 26, 27, 28, 29, 30, 31, 32, 33, 34, 35, 36, 37, 38, 39, 40, 41, 42, 43, 44, 45, 46, 47, 48, 49 or 50 cm. In one particular embodiment the scanning zone is and the scan covers 12 cm.

Attached to the transducer is a standoff pad 38, which moves the transducer over the connective tissue providing exact spatial information on the relative position of the transducer over the connective tissue.

In one embodiment the scanner serially images the connective tissue or part thereof axially 600 times over 12 cm. In other embodiments the scan obtained by the scanner may comprise 1 to 10,000 images; 10 to 2000 images; 100 to 1000 images; or 400 to 800 images. In suitable embodiments 10, 50, 100, 150, 200, 250, 300, 350, 400, 450, 500, 550, 600, 650, 700, 750, 800, 850, 900, 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, 7000, 8000, 9000 or 10,000 images may be obtained.

Once the scan has been obtained computer 10 may reconstruct the scan and quantify consistency between axial images. Accordingly and of great advantage the present invention can yield high quality images to aid diagnosis and quantify change in the connective tissue as a whole as well as in discrete sections of the connective tissue.

More importantly, the invention may guide the loading of the connective tissue as it can clearly identify and quantify response to load. With this technology, an injured connective tissue may be accurately classified as soon as it is injured, and it may be monitored during recovery and through return to load, detecting early indications that the connective tissue has not adapted to the rehabilitative load. Decisions to maintain or modify loads and/or treat as outlined herein can then be made.

Optionally, the area over the connective tissue or part thereof to be monitored or scanned may be clipped and shaved one day prior to the scan. The shaving is performed to ensure maximum contact between the skin of the subject to be scanned and the standoff pad of the scanner.

A coupling gel may also be applied to the region surrounding the connective tissue or part thereof to be scanned to further ensure maximum contact between the skin and the standoff pad.

In one embodiment tracking device 34 is placed over a suitable aspect of the connective tissue or part thereof to be scanned. For example, when scanning the superficial digital flexor tendon (SDFT) the tracking device is placed over the palmar aspect of the limb.

Preferably the region of interest of the connective tissue to be scanned is positioned in the middle of the scanning zone 36.

A standard position may be determined by beginning the scan a set distance from the ground.

Once in position, tracking device 34 may be started and transducer 32 moves distally along the connective tissue. In one embodiment tracking device moves 12 cm while capturing transverse images every 0.2 mm in a scan.

In other suitable embodiments transverse images may be captured every 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9 or 10 mm That is, suitably images may be captured every 0.01 to 10; every 0.1 to 5; or every 0.15 to 0.25 mm Preferably, the connective tissue or part thereof is held stable in the one position for sufficient time for the scan to be completed. Suitably, this time is 10 to 40 seconds. In one embodiment the scan time is fifteen seconds.

The scan may be repeated. The number of repeats obtained may be 2, 3, 4, 5, 6, 7, 8, 9, 10, 15, 20, 25, 30, 35, 40, 45, 50 or any number therebetween. Preferably the scan comprises at least one repeat.

The number of repeats obtained is preferably the number required until the quality of the scan allows for quantification of the connective tissue or part thereof.

The other limb may also be scanned. The scan of the other limb may be used for comparison and/or to detect a subclinical disease of condition.

During scanning when the subject is a horse, if the horse will not stand still on both legs, the horse may be placed in a stall with the superficial flexor tendon brought into the anatomical position in the sagittal plane and the contra lateral fore leg held in a flexed position. If required the horse may be sedated.

The acquired image of the scan may be saved. In one embodiment the scan is saved in .utc format and analysed using the software provided with the UTC imaging device.

The area of connective tissue to be analysed may be segmented on the scan and the images associated with that area may be analysed to detect any differential structural organisation. The differential structural organisation may be detected by analysing and/or quantifying the continuity.

The scan may be analysed as pixels. The acquired image of the scan may be stored and/or displayed as a series of pixels.

The series of images may be reconstructed. Reconstruction may comprise displaying two or more images of a series of images in a scan side by side relative to the position of the connective tissue or part thereof scanned.

The series of images may be quantified. The quantification may include quantifying consistency between one image or between a series of images. The consistency may be between gray values of the pixels on the grayscale.

The quantification of axial slices may not only give high quality images to aid diagnosis, but can quantify change in the connective tissue as a whole but also in discreet sections of the connective tissue.

Once the scanning procedure is complete, the scan data may be rendered for display. The rendering may include transforming the scan and images comprised therein into a 3-dimensional tomographical image of the connective tissue or part thereof.

In one embodiment of the rendering a region of interest (ROI) is selected around the contour of the pathological area of the connective tissue or part thereof.

Suitably, the ROI may be 5 mm distal and proximal to the pathological area, i.e. the ROI extends 5 mm in each extent of the connective tissue or part thereof from the identified or hypothesised pathological area. In other embodiments the ROI is 1 to 50 mm; 2 to 30 mm; or 3 to 10 mm distal and proximal to the pathological area. The ROI may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mm distal and proximal to the pathological area.

In another embodiment the ROI may comprise a number of pixels. The ROI may comprise 500, 1000, 1500, 2000, 2500, 3000, 3500, 4000, 4500 or 5000 pixels. In one embodiment the ROI comprises 2500 pixels.

The one or more region of differential structural disorganisation may be detected by analysing the stability of the scan or echopattern of this ROI. This analysis may be measured using UTC software available with the UTC scanner from UTC Imaging BV.

The analysis of the stability of the scan may quantify the overall homogeneity of the connective tissue and provide information about cellular and fibrillar components.

In one embodiment the stability of the scan may be measured by discriminating the pixels comprised in each image into four different categories: Category C—pixels that were exclusively correlated as a consequence of their constantly high gray values; which is indicative of intact fasciculi (correctly aligned fibres) showing constantly high gray values;

Category E—pixels with exclusively entropy as a consequence of their rapidly changing gray values over contiguous images; this is indicative of accumulations of cells and/or fibrils (in one embodiment the gray level variation is greater than (>) 10%);

Category B—pixels that were correlated but that also had some degree of entropy with slight variation, which is indicative of incomplete fasciculi (certain steadiness, in one embodiment the gray level varies by approximately >0-10%); or Category N—pixels that did not correlate and did not have entropy; in most cases this is indicative of homogenous accumulations of fluid or cells (in one embodiment there is no correlation of pixels).

Values may be expressed as percentages of total pixels in ROI.

In one embodiment described above, pixels with a gray level >10% are defined as category E. In other embodiments category E may be defined as >5, >15, >20, >25, >30, >35, >40, >45 or >50%.

Various display methods may be used to simplify the display of the classifications according to the invention. In one embodiment a colour coding is used. According to the colour coding each pixel is displayed in a colour coded by the category into which the pixel is assigned. In one embodiment a table may be displayed on screen 18 listing the relative amount of Category C, Category B, Category E and Category N pixels in the scan or part thereof.

In another embodiment a colour coded graph is displayed on screen 18 showing the pixels of Category C, Category B, Category E and Category N as different colours. For example, Category C pixels may be displayed as green, Category B pixels as blue, Category E pixels as Red and Category N pixels as gray. A black background may be used.

Preferably both a table and graph are displayed.

The invention may include using a reference scan. The reference scan may be a healthy connective tissue or an earlier scan of the same connective tissue. The earlier scan may be before loading.

The reference scan or colour coded graph based on the reference scan may be subtracted from the ultrasound scan or a colour coded graph based on the ultrasound scan for display purposes.

The connective tissue may then be classified according to the invention. The classification is of significant advantage over other methods because it is objective. The classification and the change in classification in response to loading and/or over time may be used to monitor the connective tissue's response to load.

The classification may be as healthy if a region of interest of the ultrasound scan comprises mostly or substantially Category C pixels.

The classification may be as reactive if a region of interest of the ultrasound scan comprises a higher level of Category E pixels or if a level of Category E pixels has increased from a baseline or earlier ultrasound scan.

The classification may be as degenerative if a region interest of the ultrasound scan comprises one or more area of Category N pixels.

A variation in the consistency of the axial scans is required to indicate a change in classification. In one embodiment the change is quantified by a variation in a ratio of categorised pixels and/or visually appraising the scan itself.

The classification of the connective tissue or part thereof may be changed if the categorization of pixels changes. The classification or a change therein may be also be made taking into account a clinical evaluation whish allows judgements about changes to the connective tissue in question.

Once the connective tissue or part thereof has been classified a composition and/or method of treatment may be selected as described below.

Treatments for Stages of Connective Tissue Pathology

Reactive

Medications: Medications that may reduce the cell activity and/or cell proliferation are indicated. Medications that reduce the protein production of the cells are also important. The medications and the amount, delivery and the length of time used are may be dependent on the assessment of the connective tissue or part thereof.

Key drugs for this stage may comprise an inhibitor of cell activity and an anti inflammatory including dexamethasone, ibuprofen and $Cu^{2+}$ ibuprofenate, doxycycline and EGCG. Medications that have a similar effect are naproxen and celecoxib and other glucocorticoids that act for longer time periods and are more efficacious. The delivery of medications may be orally, through injection (periconnective tissue) and through local application with or without a transporting substance (DMSO).

Several drugs may act to alter the natural history of this stage under the new model. Corticosteroids (in particular Dexamethasone) are potent inhibitors of proteoglycan production and of the increased cellularity that this condition can invoke. Non Steroidal anti-inflammatory drugs (in particular Ibuprofen) have effects on this proteoglycan production as well increased cellularity and cell activity. This medication may also be used after reaction has occurred and can also be used to prevent such reaction occurring in the first place.

Doxycycline has inhibitory effects on TNF alpha which is involved in acute connective tissue injury. Doxycycline also has anti matrix metalloproteinase activity which means it can lead to higher amounts of collagen within the connective tissue leading to a superior and stronger connective tissue.

EGCG which is found in green tea also has effects on TNF as well being an inhibitor of collagenase which is responsible for breaking down collagen which will weaken the connective tissue. EGCG will inhibit the breakdown of collagen. This makes it an ideal medication for treatment of both an acute and a chronic connective tissue injury.

Load: A reactive connective tissue has responded to an overload, hence reducing load is indicated. If possible, slow or isometric, heavy loads are advantageous at this stage. The length of time required for load reduction and the amount of load reduction will be different for each presentation and is best directed by clinical impression and imaging data.

Frequency of scanning: The connective tissue may be imaged daily, twice a week or weekly until connective tissue loading is introduced.

Dysrepair

Medications: Maintenance doses of those medications that may reduce cell activity and production are important, although the use of dexamethasone and other glucocorticoids is contraindicated in this stage. Ibuprofen may be the main medication at this stage. The delivery of medications at this stage may be oral or through local application.

Load: The collagen matrix may be beginning to lose structure and load to stimulate collagen production and alignment are essential. Loads that are through range initially at a slow speed and building through to faster and higher loads as tolerated and measured by the UTC are indicated.

Frequency of scanning: the connective tissue may be scanned 2 days after each increase in load. If a connective tissue becomes reactive then it may be scanned every 3 days until the reactive response has disappeared.

Change specifics: Maintenance of all parameters may be an important criteria as the load is increased. Any decrease in the ratio of category B to category E and/or category N pixels may indicate that the connective tissue has reacted to the load and the connective tissue should be unloaded for a short time until the parameters return to the pre-reactive levels. Load should then be reintroduced gradually.

Degeneration

Medications: Depending on cell activity, medications that induce a response in the connective tissue may be indicated. Autologous blood, stem cell therapy and proliferants injected into or around the connective tissue would be efficacious.

Load: depending on the preceding unloading, the connective tissue may have little load tolerance. Rehabilitation that gradually increases load capacity of the connective tissue, limb and individual, monitored by UTC imaging, may slowly improve the connective tissue's capacity. The outcome of these connective tissues depends on the time taken for rehabilitation, the integrity if the connective tissue and the loads that will be placed on it when fully recovered.

Frequency of scanning: Monthly scanning may be essential, and scanning two days after load increase may also be essential.

Change specifics: Maintenance of all parameters may be an important criteria as the load is increased. Any decrease in the ratio of category B to category D or category N pixels may indicate that the connective tissue has reacted to the load and the connective tissue should be unloaded for a short time until the parameters return to the pre-reactive levels. Load should then be reintroduced gradually.

Treatment and Prevention of Connective Tissue Injury:

As the risk factors for connective tissue injury are not well understood, it is difficult to prevent pathology developing. In those with a history of injury, it can be assumed that the connective tissue is vulnerable to the condition and using preventative loading strategies and medication is indicated.

Compositions

The invention provides various compositions that may be used for treatment of a connective tissue disease or condition.

The composition may comprise a pro-inflammatory cytokine inhibitor and an antioxidant or catechin.

The pro-inflammatory cytokine inhibitor may be an antibiotic, such as a tetracycline antibiotic and/or a macrolide antibiotic. The antibiotic may be doxycycline, erythromycin, clarythromycin and/or azithromycin.

Where the subject is a horse, in embodiments wherein the pro-inflammatory cytokine inhibitor is doxycycline, the composition may comprise 1 to 50 gram per day, 4 to 40 gram per day; or 5 to 15 gram per day. Suitably the dose may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 gram per day. In one suitable embodiment the composition comprises approximately 10 gm per day.

The antioxidant or catechin may be epigallocatechin gallate (EGCG), a green tea extract, a fish oil, a fish oil extract, epigallocatechin (EGC), epicatechin gallate (ECG), epicatechin (EC), gallocatechin (GC) and/or catechin (C). The fish oil extract may be n3-PUFA. In preferable embodiments the antioxidant or catechin is epigallocatechin gallate (EGCG) and/or a green tea extract.

The antioxidant or catechin may be an extract of a green tea. The extract may be a pure or substantially pure extract or any dilution thereof. Suitable dilutions include a 1:10-100 extract; 1:15-50 extract; or 1:20-30 extract. In one embodiment the extract is a 1:25 extract.

The composition may comprise 1 to 100 gram; 10 to 50 gram; or 20 to 30 gram of the extract of a green tea. In one embodiment the extract comprises 25 gram.

In embodiments wherein the antioxidant or catechin is EGCG, the composition may comprise 25 gm of a 1:25 extract of green tea per day or equivalent.

In embodiments wherein the antioxidant or catechin is green tea, the composition may comprise approximately 25 gm of a 1:25 green tea extract per day or equivalent.

The antioxidant or catechin may be caffeine free. Any of the antioxidants or catechins described herein may be utilised as caffeine free.

The composition may also comprise an anti-inflammatory. The anti-inflammatory may be a Non-Steroidal Anti-Inflammatory Drug (NSAID). The NSAID may be a COX 2 NSAID. The NSAID may be ibuprofen, copper ibuprofenate ($Cu^{2+}$ ibuprofen), indomethacin, copper indomethacin ($Cu^{2+}$ indomethacin), naproxen, flurbiprofen and/or celecoxib. Preferably, the anti-inflammatory is copper ibuprofenate.

In embodiments wherein the NSAID is ibuprofen or copper ibuprofenate, the composition may comprise 1 to 50 gram; 2 to 20 gram; or 6-12 gram per day or equivalent. Suitably the composition comprises 6 to 12 gram per day.

The composition may also comprise an inhibitor of cell activity. Any compound that damps down cell activity is suitable as an inhibitor of cell activity. The inhibitor of cell activity may also inhibit cell proliferation. An inhibitor of cell activity may settle down or stabilizes an overactive state of the cell. The inhibitor of cell activity may also inhibit protein production from the cell and/or inhibit production of one or more cytokines. The inhibitor of cell activity may be an antimitotic, which is a substance that inhibits cell division. However, the use of the term "antimitotic" is controversial in reference to tenocytes due to uncertainty over cell proliferation being a result of migration or cell division.

The inhibitor of cell activity may also inhibit proteoglycan production.

The inhibitor of cell activity may be a steroid. The steroid may be a glucocorticoid steroid. The glucocorticoid steroid may be dexamethasone.

Based on the teaching herein a skilled person is readily able to select a suitable dosage of the inhibitor of cell activity. When the subject is a horse, the dose may be sufficient to result in a dose of 0.05 to 1 mg/kg. In a particular embodiment the dose may be approximately 0.082 mg/kg.

It is to be understood that the anti-inflammatory, particularly a NSAID, may also be an inhibitor of cell activity. Suitably, the composition must contain both an anti-inflammatory and an inhibitor of cell activity as described herein. Generally, an inhibitor of cell-activity as described herein has a greater effect on cell activity than an anti-inflammatory.

The compositions according to the invention may also comprise an additional therapeutic such as, a proton pump inhibitor and/or a H2 antagonist. In a particular embodiment the additional therapeutic is zantac.

In one suitable embodiment, the composition comprises dexamethasone, ibuprofen, doxycycline and EGCG. This composition is suitable for and is referred to as the "Tendon Guard Intensive" composition or formulation.

The Tendon Guard Intensive composition is best utilised outside of competition and may therefore contain caffeine, i.e. there may be no requirement for caffeine-free components.

In another suitable embodiment, the composition comprises ibuprofen, doxycycline and EGCG. This composition may be used to treat connective tissue dysrepair is referred to as the "Tendon Guard Prevention" composition or formulation.

Yet another suitable embodiment is a composition comprising indomethacin, doxycycline and EGCG. This composition is suitable for administration prior to competitive racing and is referred to as the "Tendon Guard Pre-Race" composition or formulation.

Another suitable embodiment is a composition comprising doxycycline and EGCG, which is suitable for administration prior to and during competitive racing and is referred to as the "Tendon guard race" or "Tendon guard gold" composition or formulation. It is understood that during competition it may be required to use a caffeine free composition. To comply with this requirement caffeine-free EGCG may be used in the composition.

The composition of the invention may be provided in divided doses or in a once daily format.

In embodiments wherein the composition comprises a once daily format the composition may further comprise a slow release carrier or be the active ingredient attached to a salt which in one embodiment is copper, but is not limited thereto.

The pro-inflammatory cytokine inhibitor, antioxidant or catechin, anti-inflammatory and/or inhibitor of proteoglycan production or cell inhibitor may be provided as a pharmaceutically acceptable salt thereof.

The term "pharmaceutically acceptable salts" as used herein refers to salts which are toxicologically safe for systemic administration. The pharmaceutically acceptable salts may be selected from the group including alkali and alkali earth, ammonium, aluminium, copper, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, pamoate, pectinate and s-methyl methionine salts piperazine and the like.

The compositions of the invention may also comprise a pharmaceutically acceptable carrier, diluent and/or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates, and pyrogen-free water.

A useful reference describing pharmaceutically acceptable carriers, diluents and excipients is Remington's Pharmaceutical Sciences (Mack Publishing Co. N.J. USA, 1991).

Any safe route of administration may be employed for administering the compositions of the invention, including fusion proteins. For example, oral, rectal, parenteral, sublingual, buccal, intravenous, intra-articular, intra-muscular, intra-dermal, subcutaneous, inhalational, intraocular, intracerebroventricular, transdermal (topical) and the like may be employed.

Dosage forms include tablets, dispersions, suspensions, injections, solutions, syrups, troches, capsules, suppositories, aerosols, transdermal patches, douches and the like. These dosage forms may also include injecting or implanting controlled releasing devices designed specifically for this purpose or other forms of implants modified to act additionally in this fashion. Controlled release of the composition or pharmaceutical composition may be achieved by coating the same, for example, with hydrophobic polymers including acrylic resins, waxes, higher aliphatic alcohols, polylactic and polyglycolic acids, and certain cellulose derivatives such as hydroxypropylmethyl cellulose. In addition, the controlled release may be achieved by using other polymer matrices, liposomes and/or microspheres.

Pharmaceutical compositions of the present invention suitable for administration may be presented in discrete units such as vials, douches, capsules, sachets or tablets each containing a predetermined amount of one or more pharmaceutically active composition of the invention, as a powder or granules or as a solution or a suspension in an aqueous liquid, a non-aqueous liquid, an oil-in-water emulsion or a water-in-oil emulsion. Such compositions may be prepared by any of the method of pharmacy but all methods include the step of bringing into association one or more pharmaceutically active composition of the invention with the carrier which constitutes one or more necessary ingredient. In general, the compositions are prepared by uniformly and intimately admixing the agents of the invention with liquid carriers or finely divided solid carriers or both, and then, if necessary, shaping the product in to the desired presentation.

Pharmaceutical compositions of the present invention suitable for topical administration may be formulated into an ointment, lotion, salve, gel, or cream, as is generally known in the art. Typical dermal and transdermal formulations comprise a conventional aqueous or non-aqueous vehicle, for example a cream, ointment, lotion or paste or are in the form of a medicated plaster, patch or membrane.

The pro-inflammatory cytokine inhibitor, antioxidant or catechin, anti-inflammatory and/or inhibitor of proteoglycan production or a cell inhibitor of this invention may be present in an amount sufficient to treat a connective tissue disease or condition, including tendinopathy and related disorders. Suitable dosages of the compositions of the invention containing such may be readily determined by those skilled in the art.

Alternatively the pro-inflammatory cytokine inhibitor, antioxidant or catechin, anti-inflammatory and/or inhibitor of proteoglycan production or a cell inhibitor are present in an amount sufficient to prevent, inhibit or ameliorate a connective tissue disease or condition.

The above pharmaceutical compositions may be administered in a manner compatible with the dosage formulation, and in such amount as is effective to improving connective tissue disease or condition in a subject, particularly a subject suffering from an acute onset or persistent connective tissue disease or condition. The dose administered to a subject, in the context of the present invention, should be sufficient to achieve a beneficial response in a subject over time, such as improving a connective tissue disease or condition. The quantity of the pharmaceutical composition to be administered may depend on the subject to be treated, inclusive of the age, sex, weight, and general health condition thereof. In this regard, precise amounts of the pharmaceutical composition required to be administered will depend on the judgement of the clinician.

A suitable dosage of the compounds of the compositions of the invention containing such may be readily determined by those skilled in the art.

In another aspect the invention provides a method for treating a connective tissue disease or condition in a non-human subject in need thereof, the method including providing a composition as described herein to thereby treat the connective tissue disease or condition in the non-human subject.

The present inventors are the first to use the compositions described herein, and the requisite pharmaco-active substances, in equine athletes for the treatment of tendinopathy.

The invention also provides a method of designing Clinical Load Management (CLM). It is recognised that connective tissue morphology is reactive to load. This is due to changes at a cellular level. To manage these changes in equine athletes clinical experiences, the method of the invention and pharmacological intervention using the compositions and methods of the invention are required. This CLM allows equine athletes to perform at highest level possible without compromising connective tissue integrity.

The CLM may include treadmill and track volume prescription, paddock size implementation strategies and weight considerations.

The CLM may include prevention and protection, treatment and recovery and high performance racing management.

The prevention and protection may include serial monitoring and tendon guard prevention.

The treatment and recovery may include tendon guard intensive and/or tendon guard race.

The high performance racing management may include serial monitoring, clinical load management, tendon guard prevention, tendon guard pre-race.

The following non-limiting examples illustrate the invention. These examples should not be construed as limiting: the examples are included for the purposes of illustration only. The Examples will be understood to represent an exemplification of the invention.

EXAMPLES

Method of Scanning and Treatment

The method of the invention was used to scan both a healthy tendon and a tendon recovering from an injury.

A UTC scanner comprising a 10 MHz linear array transducer was used to scan a healthy horse tendon and a recovering horse tendon. A scan of 12 cm of each tendon was performed with an image acquired every 0.5 mm.

Figure 2:
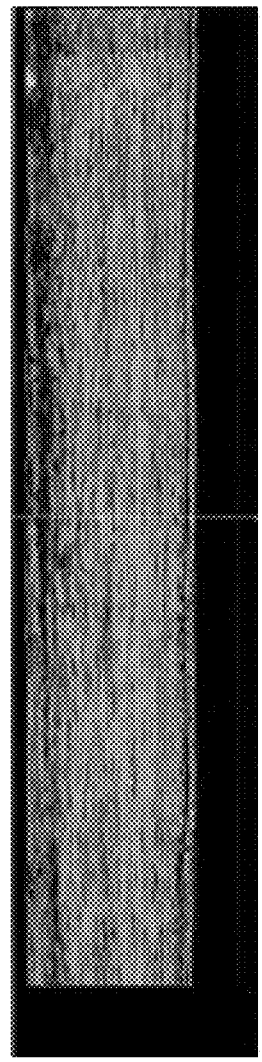
FIG. 2 shows a scans of a normal tendon produced in grayscale according to one embodiment of the invention.

FIG. 2 shows an image 200 of a scan of the healthy tendon produced according to the method of the invention.

Figure 3:
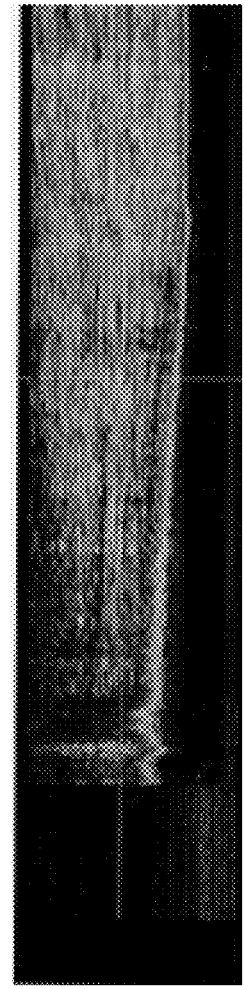
FIG. 3 shows a scans of a recovering tendon produced in grayscale according to one embodiment of the invention.

FIG. 3 shows an image 300 of a scan of the recovering tendon Image 300 shows an increase in entropy between pixels or a decrease in consistency between neighbouring pixels as compared to image 200. That is, compared to image 300, image 200 shows an increase in consistency between neighbouring pixels.

The same UTC scanner was used to scan a healthy human patella tendon prior to a compressive load being delivered via landing heavily and after the load was applied. These scans are shown in FIGS. 4A-H in grayscale and in FIGS. 5A-H in colour. FIGS. 4A-D and 5A-D show cross-sections while FIGS. 4E-H and 5E-H show sagittal sections.

Figure 4A:
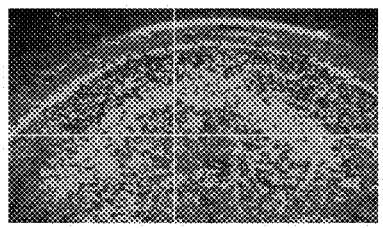
FIGS. 4A-H show scans of a tendon in grayscale according to one embodiment of the invention.
Figure 5A:

FIGS. 4A and 5A show a cross section of a region of the tendon before a compressive load has been applied. The region of interest that is being managed is near the centre of the scan, i.e. around the centre of the crosshairs.

Figure 4B:
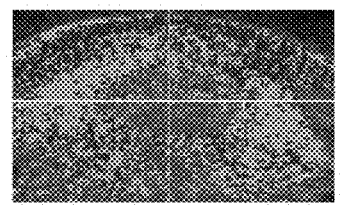
Figure 5B:
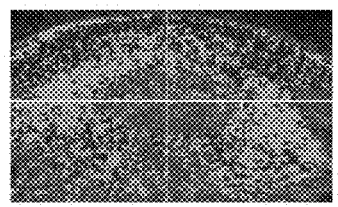

FIGS. 4B and 5B shows a cross section of the same region as shown in FIGS. 4A and 5A, after the subject has fallen on the tendon. The grayscale image of FIG. 4B shows a larger amount of darker pixels in the region of interest and the colour image of FIG. 5B shows an increase in red pixels in the region of interest. As will be apparent the increase in darker pixels and red pixels leads to a decrease in lighter pixels and green and/or blue pixels.

After observation of FIG. 4B the subject was treated with a composition according to the invention and load management.

Figure 4C:
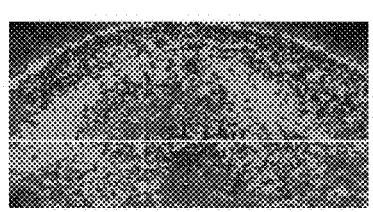
Figure 5C:
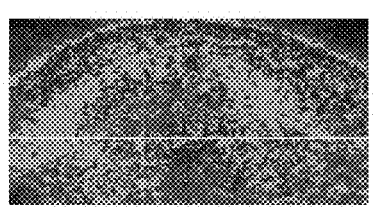

FIGS. 4C and 5C are images of a scan taken five days after the scan shown in FIGS. 4B and 5B and show the same area as shown in FIGS. 4A and 4B. FIG. 4C shows a decrease in the number of darker pixels and a corresponding increase in lighter pixels in the region of interest, which correlates to a decrease in red and increase in green and blue pixels in FIG. 5C.

Figure 4D:
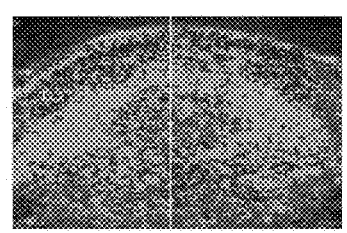
Figure 4E:
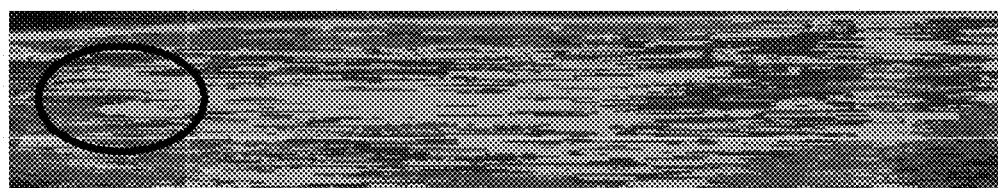
Figure 4F:
Figure 4G:
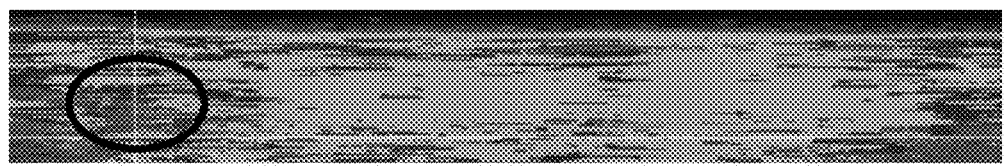
Figure 4H:
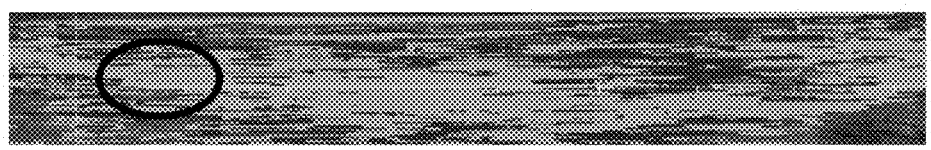
Figure 5D:
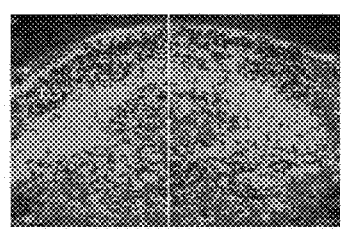
Figure 5E:
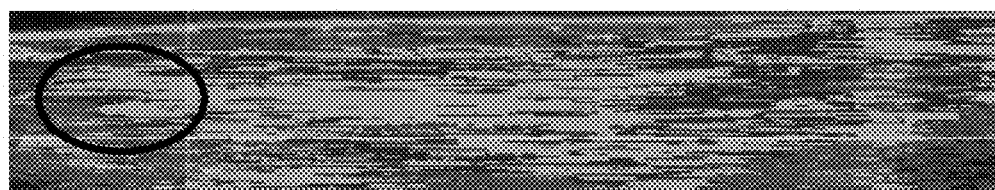
Figure 5F:
Figure 4G:
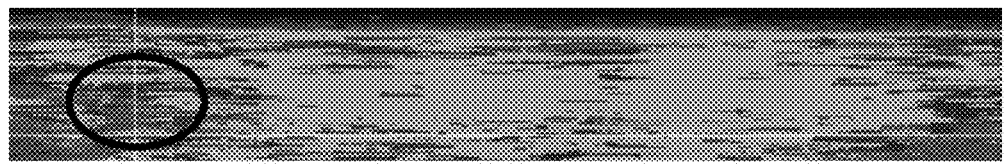
Figure 5H:

FIGS. 4D and 5D are images of a scan taken two days after the scan shown in FIGS. 4C and 5C. FIG. 4D shows a further reduction in darker pixels and further increase in lighter pixels in the region of interest. FIG. 5D shows a further reduction in red pixels and a further increase in green and blue pixels. Further, green pixels appear more abundant than blue pixels. FIGS. 4D and 5D show the tendon appears to have returned to normal and is similar to the images shown in FIGS. 4A and 5A.

FIGS. 4E-4H and 5E-5H are sagittal sections corresponding to the cross-sections of FIGS. 4A and 4B, respectively. The region of interest is shown inside the black oval.

FIGS. 4E-4H and 5E-5H show the same increase in darker pixels (grayscale) and red pixels (colour) and decrease in lighter pixels (grayscale) and green and blue pixels (colour) after application of load and then a return to normal after treatment with a composition according to the invention.

Composition and Method of Treatment

A composition comprising ibuprofen and doxycyline according to the invention was provided to a thouroughbred racing horse after a tendon injury. The horse was able to return to racing in six weeks which was unprecedented in the history of horse racing.

Further Studies of Composition and Method

The treatment of twenty (20) racing thoroughbred horses for acute tendon injury was performed at the Melbourne stable of Mr. Michael Kent (http://mckentracing.com.au/). In this treatment programme all twenty horses were treated immediately on detection of tendon injury. The injury was then confirmed by ultrasound using a Ultrasonic Tissue Characterisation, which is more sensitive than conventional ultrasound techniques and can detect very subtle changes in tendon structure, which makes it more able to detect the efficacy of a given tendon treatment.

The treatment given to the twenty (20) horses comprised a formulation named "Tendon Guard Intense", which consisted of 30 gm of treatment twice per day by oral paste via syringe. The formulation consisted of three (3) active compounds:

Ibuprofen 167 mg/gm;
Doxycycline 167 mg/gm; and
Green Tea Extract 163 mg/gm.

All horses were given daily treatment and were put immediately back into light exercise within two (2) weeks of injury. Ordinarily any exercise would lead to a worsening of injury with any other method if trained so early after an injury. This medication was continued to be given before and after racing, only stopping for 3-5 days at a time so as to stay within the regulations of the relevant racing authorities.

All the horses were also treated with a "Tendon Guard Race" formulation leading up to racing. This Race Formulation consisted of Doxycycline 5 Gm and Green Tea Extract 5 Gm and was given twice daily.

All twenty (20) horses made a successful return to racing within six (6) months. Remarkably, all horses ran at a similar level to before their injury occurred. After treatment and return to racing, three of the twenty (20) horses won at graded stakes level. This was a standard not achieved prior to the injury occurring. These racing wins meant that all three (3) of these horses were able to improve post injury.

All treated horses ran at least five (5) times and just as importantly none were reinjured whilst on the treatment.

Figure 6:
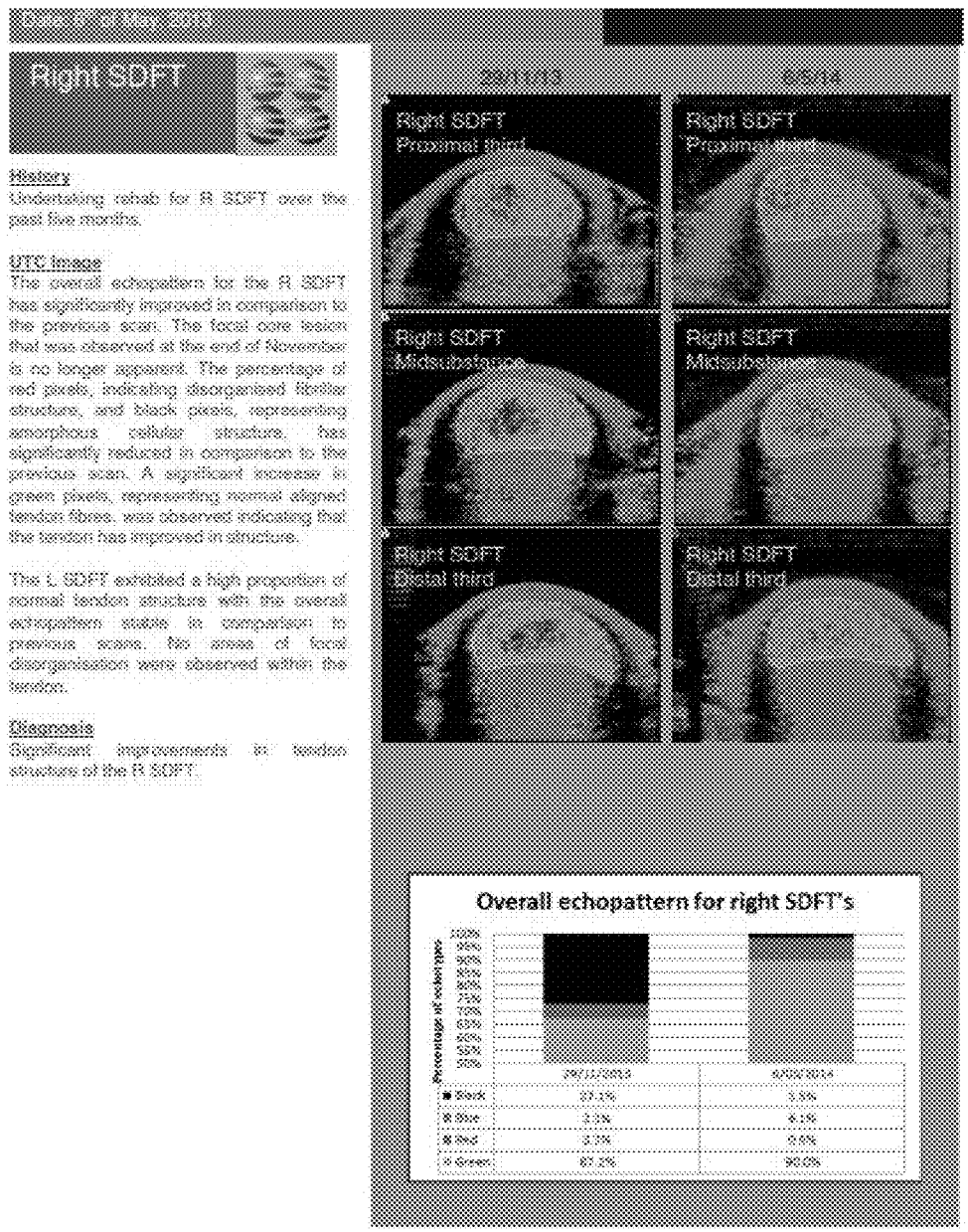
FIG. 6 dated 6 May 2013, shows comparative scans of the right Superficial Digital Flexor Tendon (SDFT) before treatment as part of the cohort of twenty (20) described above (left hand column dated 29 Nov. 2013) and after treatment (right hand column dated Jun. 5, 2014).
Figure 7:
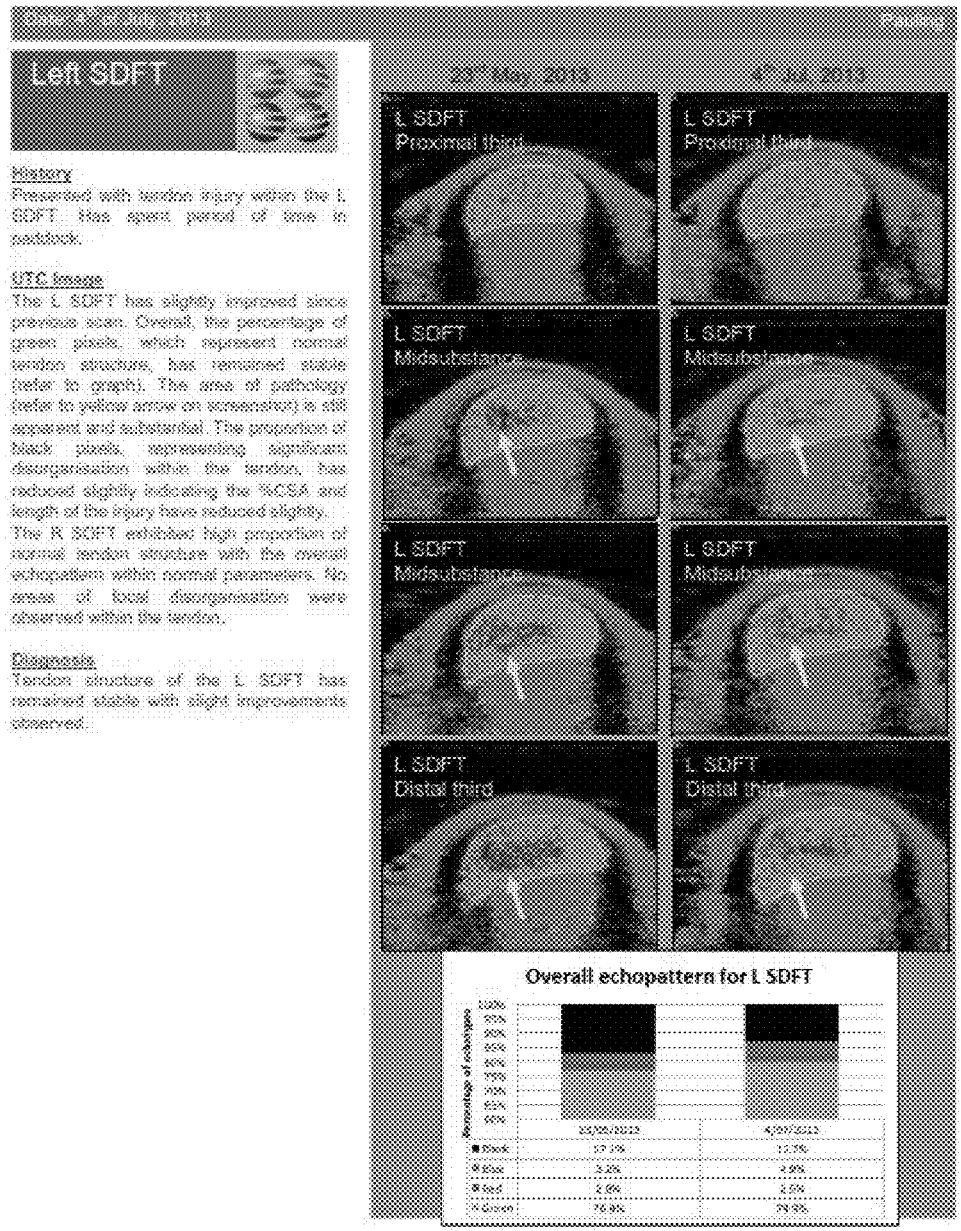
FIG. 7 dated 4 Jul. 2015, shows comparative scans of the SDFT of a second horse, also part of the cohort of twenty (20) described above. The left hand column show scans before treatment which show a tendon injury within the left SDFT. The right hand column of scans shows an improvement with the above-described treatment.

FIGS. 6 and 7 quantify the improvement achieved with the invention. FIG. 6, dated 6 May 2013, shows comparative scans of the right Superficial Digital Flexor Tendon (SDFT) before treatment as part of the cohort of twenty (20) described above (left hand column dated 29 Nov. 2013) and after treatment (right hand column dated Jun. 5, 2014). The right hand scans show a dramatic improvement in tendon structure as described in the specification as filed. The overall echopattern has significantly improved, the focal core lesion is no longer present and the percentage of red pixels (indicating disorganized fibrillar structure) and black pixels (indicating amorphous cellular structure) has significantly reduced in comparison to the previous scan of the same horse. A corresponding increase in green pixels (indicating normal aligned tendon fibres) was observed indicating that the tendon has improved in structure.

The second scan, dated 4 Jul. 2015, shows comparative scans of the SDFT of a second horse, also part of the cohort of twenty (20) described above. The left hand column show scans before treatment which show a tendon injury within the left SDFT. The right hand column of scans shows an improvement with the above-described treatment. As part of the improvement, the proportion of black pixels has reduced slightly, which indicates that the percentage cross section area (% CSA) of the injury and the length of the injury have reduced.

These results are a significant improvement over conventional treatments. For example, in a comparative study by Gillis ("Rehabilitation of Tendon and Ligament Injuries", Gillis, Carol, L., Proceedings of the Annual Convention of the AAEP; 1997:43: pages 306 to 309; see: http://www.e-quinepartnersamerica.com/research/Gillis-RehabTendons-LigamentsAAEP.pdf) in which fifty horses with tendon injury treated with traditional rehabilitation methods without any medication were reviewed, only twenty six (26) were able to make a successful return to racing. Racing was defined as completing five (5) or more races. This amounted to only a 52% success rate. Additionally, these fifty (50) horses had extensive rehabilitation times of 8-9 months prior to racing.

A skilled person in the art in 2013 would have treated a horse with tendon injury conservatively (exercise alone) or with injection of stem cells or PRP (Platelet Rich Plasma) These injection therapies are given to purportedly enhance tendon healing as its dogma that the mechanism of injury is tearing of collagen fibres. The inventors have shown that the first mechanism of injury is that tendon cells actually overproduce proteoglycan. Ibuprofen is specifically given to dampen this proteoglycan overproduction. Doxycycline and Green Tea (EGCG) are given as immune modulators and as metalloproteinase inhibitors. Given that the clear previous understanding has been the tendon is torn (and indeed has a hole in it) there would be no logical reason for anyone skilled in the art to treat with any of the medications, Ibuprofen, Doxycycline and Green Tea or EGCG before provision of this invention.

An acute tendon injury in a horse, is also known as a "Bowed Tendon". This injury is clinically characterized by visible swelling of the tendon, heat to touch, as well as pain on palpation of the tendon. Clinical improvement of such a tendon injury is manifest by the diminution and ultimate absence of any swelling, heat and pain on palpation.

The trials detailed above were carried out using the "polypaste" (multiple medications) approach to tendon injury in horses using "Tendon Guard Intense". Three medications were used in initial tendon injury treatment: a proinflammatory cytokine inhibitor (Doxycycline 5 gm BD), an antioxidant or catechin (Green Tea extract/EGCG 5 gm BD) and an anti-inflammatory (Ibuprofen 5 gm BD). Throughout the testing process, a cohort of horses, were unable to take all of the individual ingredients planned, due to a number of reasons:

a. Doxycycline was sometimes contraindicated because the trainer or vet wished not to use an antibiotic, due to the theoretical risks of gastrointestinal upset, in particular the feared and potentially deadly complication of antibiotic induced colitis in a horse.

b. Green Tea Extract/EGCG was not used in another circumstance because it contains extremely small levels of caffeine and individual race horse trainers didn't wish to run any risk of a raceday positive test to a banned substance above the allowable threshold.

c. Ibuprofen was most often contraindicated due to the horse suffering from suspected gastric ulcers, which precluded the use of an anti-inflammatory drug.

The individual medication contraindications outlined, led to a cohort of horses in initial testing who consequently only received a single drug or a combination of two drugs (not three) to treat their acute tendon injury. These horses received either:

i. A pro inflammatory cytokine inhibitor (Doxycline 5 gm BD) as a single agent;

ii. An antioxidant or catechin (Green Tea Extract/EGCG 5 gm BD) as a single agent;

iii. An anti-inflammatory (Ibuprofen 5 gm BD) as a single agent;

iv. A pro inflammatory cytokine inhibitor (Doxycycline 5 gm BD) plus an antioxidant or catechin (Green Tea Extract/EGCG 5 gm BD);

v. A pro inflammatory cytokine inhibitor (Doxycycline 5 gm BD) plus an anti-inflammatory (Ibuprofen 5 gm BD); or vi. An antioxidant or catechin (Green Tea Extract/EGCG 5 gm BD) plus an anti-inflammatory (Ibuprofen 5 gm BD)

All horses were carefully examined daily following acute injury and after institution of medication, by either an experienced veterinarian or trainer, for the presence of all of swelling, heat and pain on palpation of the tendon. A positive clinical response to treatment was defined as the absence of all three of swelling, heat and pain on palpation. The time from medication institution until disappearance of all three signs of swelling, heat and pain on palpation was recorded, as this was deemed the ultimate marker of clinical improvement of the tendon injury. Horses were immediately put back into light exercise once these acute signs had disappeared.

PRO INFLAMMATORY CYTOKINE INHIBITOR (Doxycycline): six (6) horses were treated with Doxycycline alone (5 gms BD). The time in days until a positive clinical response (defined as disappearance of all three (3) signs: swelling, heat and pain on palpation) following medication institution for an acute tendon injury is shown in Table 1 below.

TABLE 1

Response to treatment with PRO INFLAMMATORY CYTOKINE INHIBITOR alone

| Horse | Horse Description | Place of Treatment | Treatment Started | Time until Clinical Response |
|---|---|---|---|---|
| 1 | 3 yr old gelding | Flemington Victoria | November 2009 | 28 days |
| 2 | 4 yr old gelding | Flemington Victoria | December 2009 | 27 days |
| 3 | 6 yr old gelding | Flemington Victoria | May 2010 | 21 days |
| 4 | 5 yr old mare | Flemington Victoria | August 2010 | 24 days |
| 5 | 4 yr old gelding | Flemington Victoria | January 2011 | 27 days |

TABLE 1-continued

Response to treatment with PRO INFLAMMATORY CYTOKINE INHIBITOR alone

| Horse | Horse Description | Place of Treatment | Treatment Started | Time until Clinical Response |
|---|---|---|---|---|
| 6 | 5 yr old gelding | Flemington Victoria | July 2011 | 21 days |
| Mean | | | | (24.66 days) until a positive clinical response to treatment. |

ANTIOXIDANT OR CATECHIN: five (5) horses were treated with EGCG alone (5 gms BD). The time in days until a positive clinical response (defined as disappearance of all three signs: swelling, heat and pain on palpation) following medication institution for an acute tendon injury is shown in Table 2.

TABLE 2

Response to treatment with ANTIOXIDANT OR CATECHIN alone

| Horse | Horse Description | Place of Treatment | Treatment Started | Time until Clinical Response |
|---|---|---|---|---|
| 1 | 5 yr old gelding | Camperdown Victoria | June 2009 | 21 days |
| 2 | 3 yr old gelding | Camperdown Victoria | March 2010 | 24 days |
| 3 | 3 yr old gelding | Camperdown Victoria | October 2010 | 21 days |
| 4 | 5 yr old gelding | Camperdown Victoria | October 2011 | 28 days |
| 5 | 3 yr old gelding | Camperdown Victoria | December 2011 | 31 days |
| Mean | | | | (25 days) until a positive clinical response to treatment |

ANTI-INFLAMMATORY (Ibuprofen): eight (8) horses were treated with Ibuprofen alone (5 gm BD). The time in days until a positive clinical response, defined as disappearance of all three (3) signs: swelling, heat and pain on palpation, following medication institution for an acute tendon injury is shown in Table 3.

TABLE 3

Response to treatment with ANTI-INFLAMMATORY alone

| Horse | Horse Description | Place of Treatment | Treatment Started | Time until Clinical Response |
|---|---|---|---|---|
| 1 | 4 yr old gelding | Moe Victoria | May 2009 | 27 days |
| 2 | 4 yr old gelding | Moe Victoria | July 2009 | 24 days |
| 3 | 8 yr old gelding | Moe Victoria | November 2009 | 19 days |
| 4 | 4 yr old mare | Moe Victoria | January 2010 | 20 days |
| 5 | 6 yr old gelding | Moe Victoria | November 2010 | 25 days |
| 6 | 5 yr old mare | Moe Victoria | January 2011 | 19 days |

TABLE 3-continued

Response to treatment with ANTI-INFLAMMATORY alone

| Horse | Horse Description | Place of Treatment | Treatment Started | Time until Clinical Response |
|---|---|---|---|---|
| 7 | 3 yr old gelding | Moe Victoria | April 2011 | 18 days |
| 8 | 4 yr old gelding | Moe Victoria | April 2011 | 23 days |
| Mean | | | | (21.9 days) until a positive clinical response to treatment |

PRO INFLAMMATORY CYTOKINE INHIBITOR (Doxycycline) PLUS AN ANTIOXIDANT OR CATECHIN (Green Tea Extract/EGCG): four (4) horses were treated with Doxycycline 5 gm BD and EGCG 5 gm BD. The time in days until a positive clinical response, defined as disappearance of all three (3) signs: swelling, heat and pain on palpation, following medication institution for an acute tendon injury is shown in Table 4.

TABLE 4

Response to treatment with PRO INFLAMMATORY CYTOKINE INHIBITOR and AN ANTIOXIDANT OR CATECHIN

| Horse | Horse Description | Place of Treatment | Treatment Started | Time until Clinical Response |
|---|---|---|---|---|
| 1 | 4 yr old gelding | Camperdown Victoria | October 2009 | 26 days |
| 2 | 4 yr old mare | Camperdown Victoria | January 2010 | 17 days |
| 3 | 7 yr old gelding | Camperdown Victoria | July 2010 | 18 days |
| 4 | 4 yr old gelding | Camperdown Victoria | October 2010 | 21 days |
| Mean | | | | (20.50 days) until a positive clinical response to treatment |

PRO INFLAMMATORY CYTOKINE INHIBITOR (Doxycycline) PLUS AN ANTI-INFLAMMATORY (Ibuprofen): six (6) horses were treated with Doxycycline 5 gm BD and Ibuprofen 5 gm BD. The time in days until a positive clinical response, defined as disappearance of all three (3) signs: swelling, heat and pain on palpation, following medication institution for an acute tendon injury is shown in Table 5.

TABLE 5

Response to treatment with PRO INFLAMMATORY CYTOKINE INHIBITOR and ANT-INFLAMMATORY

| Horse | Horse Description | Place of Treatment | Treatment Started | Time until Clinical Response |
|---|---|---|---|---|
| 1 | 4 yr old gelding | Cranbourne Victoria | August 2009 | 17 days |
| 2 | 5 yr old mare | Cranbourne Victoria | December 2009 | 21 days |
| 3 | 7 yr old gelding | Cranbourne Victoria | May 2010 | 18 days |

TABLE 5-continued

Response to treatment with PRO INFLAMMATORY
CYTOKINE INHIBITOR and ANT-INFLAMMATORY

| Horse | Horse Description | Place of Treatment | Treatment Started | Time until Clinical Response |
|---|---|---|---|---|
| 4 | 4 yr old mare | Cranbourne Victoria | October 2010 | 15 days |
| 5 | 5 yr old gelding | Cranbourne Victoria | November 2010 | 15 days |
| 6 | 6 yr old gelding | Cranbourne Victoria | November 2010 | 16 days |
| Mean | | | | (17 days) until a positive clinical response to treatment |

AN ANTIOXIDANT OR CATECHIN (Green Tea Extract/EGCG) PLUS AN ANTI-INFLAMMATORY (Ibuprofen): four (4) horses were treated with EGCG 5 gm BD and Ibuprofen 5 gm BD. The time in days until a positive clinical response, defined as disappearance of all three (3) signs: swelling, heat and pain on palpation, following medication institution for an acute tendon injury is shown in Table 6.

TABLE 6

Response to treatment with AN ANTIOXIDANT
OR CATECHIN and AN ANTI-INFLAMMATORY

| Horse | Horse Description | Place of Treatment | Treatment Started | Time until Clinical Response |
|---|---|---|---|---|
| 1 | 3 yr old gelding | Angaston Sth Australia | November 2009 | 19 days |
| 2 | 5 yr old mare | Angaston Sth Australia | January 2010 | 21 days |
| 3 | 5 yr old gelding | Angaston Sth Australia | March 2010 | 18 days |
| 4 | 4 yr old gelding | Angaston Sth Australia | November 2010 | 16 days |
| Mean | | | | (18.5 days) until a positive clinical response to treatment |

The treatment with three active components of a PRO INFLAMMATORY CYTOKINE INHIBITOR, an ANTI-OXIDANT OR CATECHIN and an ANTI-INFLAMMATORY (Doxycycline 5 gm BD/EGCG 5 gm BD/Ibuprofen 5 gm BD cohort), was discussed in Paragraphs 4 to 13. Table 7 shows the time in days until a positive clinical response, defined as disappearance of all three signs: swelling, heat and pain on palpation, following medication institution for an acute tendon injury and thereby allows a direct comparison and qualitative indication of the surprising effects of the Tendon Guard Intense composition.

TABLE 7

Response to treatment with the three
active components of a PRO INFLAMMATORY
CYTOKINE INHIBITOR, an ANTIOXIDANT OR
CATECHIN and an ANTI-INFLAMMATORY

| Horse | Horse Description | Place of Treatment | Treatment Started | Time until Clinical Response |
|---|---|---|---|---|
| 1 | 4 yr old mare | Cranbourne Victoria | October 2009 | 10 days |
| 2 | 3 yr old gelding | Cranbourne Victoria | November 2009 | 11 days |
| 3 | 6 yr old gelding | Cranbourne Victoria | February 2010 | 7 days |
| 4 | 4 yr old gelding | Cranbourne Victoria | June 2010 | 9 days |
| 5 | 5 yr old gelding | Cranbourne Victoria | September 2010 | 8 days |
| 6 | 6 yr old mare | Cranbourne Victoria | October 2010 | 12 days |
| 7 | 5 yr old gelding | Cranbourne Victoria | February 2011 | 13 days |
| 8 | 3 yr old gelding | Cranbourne Victoria | March 2011 | 11 days |
| 9 | 4 yr old gelding | Cranbourne Victoria | September 2011 | 8 days |
| 10 | 4 yr old mare | Cranbourne Victoria | November 2011 | 11 days |
| 11 | 3 yr old gelding | Cranbourne Victoria | January 2012 | 9 days |
| 12 | 4 yr old gelding | Cranbourne Victoria | April 2012 | 9 days |
| 13 | 6 yr old gelding | Cranbourne Victoria | July 2012 | 7 days |
| 14 | 3 yr old gelding | Cranbourne Victoria | September 2012 | 10 days |
| 15 | 5 yr old gelding | Cranbourne Victoria | September 2012 | 6 days |
| 16 | 4 yr old mare | Cranbourne Victoria | November 2012 | 12 days |
| 17 | 4 yr old gelding | Cranbourne Victoria | February 2013 | 10 days |
| 18 | 6 yr old gelding | Cranbourne Victoria | April 2013 | 8 days |
| 19 | 4 yr old gelding | Cranbourne Victoria | May 2013 | 10 days |
| 20 | 4 yr old gelding | Cranbourne Victoria | November 2013 | 12 days |
| Mean | | | | (9.65 days) until a positive clinical response to treatment |

The cohort of horses given Tendon Guard Intense showed a dramatic clinical improvement which enabled the 100% return to successful racing detailed above.

One additional horse was given only one third of the dose of the Tendon Guard Intense composition discussed above. The tendon in this horse took approximately three (3) weeks to settle. This horse was a five (5) year old gelding treated at Camperdown Victoria in May 2014. Instead of giving the normal dose of 30 gm BD, a stable hand gave 20 gm daily of "Tendon Guard Intense" which resulted. This tendon subsequently took twenty-three days until a clinical response, absence of all of swelling, heat and pain on palpation. The greatly increased time, compared to the determined mean of 9.65 days, led to the mistake of under-dosage being detected.

Additional Studies of Composition and Method
Anti-Inflammatories:
Additional studies have been performed with alternative anti-inflammatories and alternative NSAIDs. It is desirable to avoid using ibuprofen. The reason is ibuprofen stores in tissue and causes positive drug tests in racing horses. Copper indomethacin (CuIndomethacin) has been used as the anti-inflammatory and/or NSAID.

Doses of NSAID:

One of the advantages of CuIndomethacin is that it can be used in lower dosages. A dose of 200 mg (⅕ gram) has been used. It is hypothesized that a therapeutic effect may be achieved with 50 mg or ¼ of the usual dose or less by way of example.

Pro Inflammatory Cytokine Inhibitor:

In some embodiments, it is desirable to avoid using Doxycycline. The reason for this is that there is a worldwide push not to use antibiotics for purposes which are not infection related. For this reason, in som embodiments, curcumin, which is also a proinflammatory cytokine inhibitor, has been used at a dose of 450 mg/day with great success.

Dose of Proinflammatory Cytokine Inhibitor:

Doxycycline has been used at between 5 and 10 gram. Curcumin has been used at a dose of 450 mg. Suitable ranges are 50 mg to 20 g or 50 mg to 50 g.

Anti-Oxidant or Catechin:

It has been found that some green tea extracts contain miniscule amounts of caffeine, which can cause a positive test in racing horses. In view of this, in some embodiments, EGCG is preferred to a green tea extract.

Combination: The combination of CuIndomethacin, doxycycline and EGCG has been used with equal results in resolution of pain and swelling to the combination of ibuprofen, doxycycline and EGCG. It has been found that CuIndomethacin may be substituted for Ibuprofen with no downside to performance.

The combination of CuIndomethacin, curcumin, EGCG has also been used with similar effect.

Curcumin Substituted as an Antioxidant:

A combination of CuIndomethacin, doxycycline and curcumin has also been tested and evaluated which was found to be similarly is effective.

The present invention uses ground breaking imaging technology to monitor changes in a connective tissue. The present invention makes it possible to monitor changes in a connective tissue as it responds to load. The invention also enables screening of a connective tissue to monitor and classify the connective tissue into one of the stages described herein.

Of significant advantage, the invention can guide the loading of the connective tissue as it can clearly identify and quantify response to load. With this technology, an injured connective tissue can be accurately classified as soon as it is injured, and it can be monitored during recovery and through return to load, detecting early indications that the connective tissue has not adapted to the rehabilitative load. Decisions to maintain or modify loads can then be made.

The compositions of the invention, comprising a pro-inflammatory cytokine inhibitor and an antioxidant or catechin have not previously been applied to non-human performance animals. In part, this was due to a misunderstanding of connective tissue physiology and pathology.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. Fallon, K., Purdam, C., Cook, J., and Lovell, G., A 'polypill' for acute tendon pain in athletes with tendinopathy, 2008, Journal of Sports Science and Medicine in Sport, 11, 235-8.

The invention claimed is:

1. A method for treating a non-hemorrhoidal reactive tendinopathy where inflammation and collagen tearing is not occurring or a non-hemorrhoidal acute reactive tendon injury where inflammation and collagen tearing is not occurring in a horse in need thereof, the method comprising:
administering to the horse a composition comprising a pro-inflammatory cytokine inhibitor, an antioxidant or catechin, and an anti-inflammatory to thereby treat the non-hemorrhoidal reactive tendinopathy or the non-hemorrhoidal acute reactive tendon injury in the horse, wherein the anti-inflammatory comprises copper indomethacin, the proinflammatory cytokine inhibitor comprises curcumin and the antioxidant or catechin comprises green tea extract or epigallocatechin gallate (EGCG).

2. The method of claim 1, wherein the composition further comprises an inhibitor of cell activity.

3. The method of claim 2, wherein the inhibitor of cell activity comprises a compound that damps down cell activity, inhibits cell proliferation, settles down or stabilizes an overactive state of a cell, inhibits protein production from the cell, inhibits production of one or more cytokines, comprises an antimitotic or inhibits proteoglycan production.

4. The method of claim 2, wherein the inhibitor of cell activity comprises a steroid or a glucocorticoid steroid.

5. The method of claim 1, wherein the pro-inflammatory cytokine inhibitor, the antioxidant or catechin and the anti-inflammatory are present at amounts effective to treat the non-hemorrhoidal reactive tendinopathy or the non-hemorrhoidal acute reactive tendon injury.

6. The method of claim 1, wherein the green tea extract is pure.

7. The method of claim 1, wherein the pro-inflammatory cytokine inhibitor is provided in a dosage range of 1 to 50 g per day.

8. The method of claim 1, wherein the anti-inflammatory is provided in a dosage range of 1 to 50 g per day.

9. The method of claim 1, wherein the antioxidant or catechin is caffeine free.

10. The method of claim 1, wherein the method of treatment achieves or causes an absence of swelling, heat and pain on palpation.

11. The method of claim 1, wherein the composition is administered orally to the horse.

* * * * *